United States Patent
Malackowski et al.

(10) Patent No.: US 12,408,998 B2
(45) Date of Patent: Sep. 9, 2025

(54) OBSTACLE AVOIDANCE TECHNIQUES FOR SURGICAL NAVIGATION

(71) Applicant: Stryker Corporation, Kalamazoo, MI (US)

(72) Inventors: Donald W. Malackowski, Schoolcraft, MI (US); Joseph Bos, Kalamazoo, MI (US); Richard Thomas DeLuca, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 780 days.

(21) Appl. No.: 17/564,717

(22) Filed: Dec. 29, 2021

(65) Prior Publication Data

US 2022/0117682 A1  Apr. 21, 2022

Related U.S. Application Data

(63) Continuation of application No. PCT/US2020/040717, filed on Jul. 2, 2020.

(60) Provisional application No. 62/870,284, filed on Jul. 3, 2019.

(51) Int. Cl.
*A61B 34/30* (2016.01)
*A61B 34/00* (2016.01)
*A61B 34/20* (2016.01)

(52) U.S. Cl.
CPC .............. *A61B 34/30* (2016.02); *A61B 34/20* (2016.02); *A61B 34/70* (2016.02); *A61B 2034/2055* (2016.02)

(58) Field of Classification Search
CPC .......... A61B 34/30; A61B 34/20; A61B 34/70

USPC ........................................................ 606/1
See application file for complete search history.

(56) References Cited

U.S. PATENT DOCUMENTS

| | | |
|---|---|---|
| 4,962,463 A | 10/1990 | Crossno et al. |
| 5,603,318 A | 2/1997 | Heilbrun et al. |
| 5,715,836 A | 2/1998 | Kliegis et al. |
| 5,765,561 A | 6/1998 | Chen et al. |

(Continued)

FOREIGN PATENT DOCUMENTS

| | | |
|---|---|---|
| CN | 101254103 A | 9/2008 |
| CN | 103083089 A | 5/2013 |

(Continued)

OTHER PUBLICATIONS

English language abstract for JP 2018-506352 A extracted from espacenet.com database on Mar. 10, 2023, 2 pages.

(Continued)

*Primary Examiner* — Nadia A Mahmood
(74) *Attorney, Agent, or Firm* — Howard & Howard Attorneys PLLC

(57) ABSTRACT

Systems and methods are described herein wherein a localizer is configured to detect a position of a first object and a vision device is configured to generate a depth map of surfaces near the first object. A virtual model corresponding to the first object is accessed, and a positional relationship between the localizer and the vision device in a common coordinate system is identified. An expected depth map of the vision device is then generated based on the detected position of the first object, the virtual model, and the positional relationship. A portion of the actual depth map that fails to match the expected depth map is identified, and a second object is recognize based on the identified portion.

24 Claims, 10 Drawing Sheets

(56) References Cited

U.S. PATENT DOCUMENTS

| | | |
|---|---|---|
| 5,817,005 A | 10/1998 | Cohen |
| 5,820,623 A | 10/1998 | Ng |
| 5,824,085 A | 10/1998 | Sahay et al. |
| 5,871,018 A | 2/1999 | Delp et al. |
| 5,880,976 A | 3/1999 | DiGioia, III et al. |
| 5,882,206 A | 3/1999 | Gillio |
| 5,891,157 A | 4/1999 | Day et al. |
| 5,950,629 A | 9/1999 | Taylor et al. |
| 5,952,796 A | 9/1999 | Colgate et al. |
| 5,971,976 A | 10/1999 | Wang et al. |
| 5,976,156 A | 11/1999 | Taylor et al. |
| 5,995,738 A | 11/1999 | DiGioia, III et al. |
| 6,002,859 A | 12/1999 | DiGioia, III et al. |
| 6,021,343 A | 2/2000 | Foley et al. |
| 6,033,415 A | 3/2000 | Mittelstadt et al. |
| 6,037,927 A | 3/2000 | Rosenberg |
| 6,063,095 A | 5/2000 | Wang et al. |
| 6,097,168 A | 8/2000 | Katoh et al. |
| 6,102,850 A | 8/2000 | Wang et al. |
| 6,157,873 A | 12/2000 | DeCamp et al. |
| 6,205,411 B1 | 3/2001 | DiGioia, III et al. |
| 6,228,089 B1 | 5/2001 | Wahrburg |
| 6,233,504 B1 | 5/2001 | Das et al. |
| 6,236,875 B1 | 5/2001 | Bucholz et al. |
| 6,236,906 B1 | 5/2001 | Muller |
| 6,304,050 B1 | 10/2001 | Skaar et al. |
| 6,311,100 B1 | 10/2001 | Sarma et al. |
| 6,314,312 B1 | 11/2001 | Wessels et al. |
| 6,322,567 B1 | 11/2001 | Mittelstadt et al. |
| 6,329,778 B1 | 12/2001 | Culp et al. |
| 6,330,837 B1 | 12/2001 | Charles et al. |
| 6,336,931 B1 | 1/2002 | Hsu et al. |
| 6,341,231 B1 | 1/2002 | Ferre et al. |
| 6,347,240 B1 | 2/2002 | Foley et al. |
| 6,351,659 B1 | 2/2002 | Vilsmeier |
| 6,351,661 B1 | 2/2002 | Cosman |
| 6,368,330 B1 | 4/2002 | Hynes et al. |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,405,072 B1 | 6/2002 | Cosman |
| 6,408,253 B2 | 6/2002 | Rosenberg et al. |
| 6,413,264 B1 | 7/2002 | Jensen et al. |
| 6,414,711 B2 | 7/2002 | Arimatsu et al. |
| 6,421,048 B1 | 7/2002 | Shih et al. |
| 6,423,077 B2 | 7/2002 | Carol et al. |
| 6,430,434 B1 | 8/2002 | Mittelstadt |
| 6,432,112 B2 | 8/2002 | Brock et al. |
| 6,434,415 B1 | 8/2002 | Foley et al. |
| 6,434,507 B1 | 8/2002 | Clayton et al. |
| 6,436,107 B1 | 8/2002 | Wang et al. |
| 6,450,978 B1 | 9/2002 | Brosseau et al. |
| 6,456,868 B2 | 9/2002 | Saito et al. |
| 6,461,372 B1 | 10/2002 | Jensen et al. |
| 6,466,815 B1 | 10/2002 | Saito et al. |
| 6,473,635 B1 | 10/2002 | Rasche |
| 6,490,467 B1 | 12/2002 | Bucholz et al. |
| 6,491,702 B2 | 12/2002 | Heilbrun et al. |
| 6,494,882 B1 | 12/2002 | Lebouitz et al. |
| 6,501,997 B1 | 12/2002 | Kakino |
| 6,511,418 B2 | 1/2003 | Shahidi et al. |
| 6,514,082 B2 | 2/2003 | Kaufman et al. |
| 6,514,259 B2 | 2/2003 | Picard et al. |
| 6,520,228 B1 | 2/2003 | Kennedy et al. |
| 6,522,906 B1 | 2/2003 | Salisbury, Jr. et al. |
| 6,533,737 B1 | 3/2003 | Brosseau et al. |
| 6,535,756 B1 | 3/2003 | Simon et al. |
| 6,542,770 B2 | 4/2003 | Zylka et al. |
| 6,620,174 B2 | 9/2003 | Jensen et al. |
| 6,665,554 B1 | 12/2003 | Charles et al. |
| 6,676,669 B2 | 1/2004 | Charles et al. |
| 6,699,177 B1 | 3/2004 | Wang et al. |
| 6,704,694 B1 | 3/2004 | Basdogan et al. |
| 6,711,432 B1 | 3/2004 | Krause et al. |
| 6,723,106 B1 | 4/2004 | Charles et al. |
| 6,724,922 B1 | 4/2004 | Vilsmeier |
| 6,728,599 B2 | 4/2004 | Wang et al. |
| 6,757,416 B2 | 6/2004 | Kleiman et al. |
| 6,757,582 B2 | 6/2004 | Brisson et al. |
| 6,778,867 B1 | 8/2004 | Ziegler et al. |
| 6,785,572 B2 | 8/2004 | Yanof et al. |
| 6,785,593 B2 | 8/2004 | Wang et al. |
| 6,788,999 B2 | 9/2004 | Green |
| 6,793,653 B2 | 9/2004 | Sanchez et al. |
| 6,804,547 B2 | 10/2004 | Pelzer et al. |
| 6,815,659 B2 | 11/2004 | Cartlidge |
| 6,827,723 B2 | 12/2004 | Carson |
| 6,837,892 B2 | 1/2005 | Shoham |
| 6,850,794 B2 | 2/2005 | Shahidi |
| 6,858,003 B2 | 2/2005 | Evans et al. |
| 6,871,117 B2 | 3/2005 | Wang et al. |
| 6,892,112 B2 | 5/2005 | Wang et al. |
| 6,929,606 B2 | 8/2005 | Ritland |
| 6,951,538 B2 | 10/2005 | Ritland |
| 6,963,792 B1 | 11/2005 | Green |
| 6,978,166 B2 | 12/2005 | Foley et al. |
| 6,999,852 B2 | 2/2006 | Green |
| 7,006,895 B2 | 2/2006 | Green |
| 7,035,716 B2 | 4/2006 | Harris et al. |
| 7,043,961 B2 | 5/2006 | Pandey et al. |
| 7,050,845 B2 | 5/2006 | Vilsmeier |
| 7,055,789 B2 | 6/2006 | Libbey et al. |
| 7,056,123 B2 | 6/2006 | Gregorio et al. |
| 7,097,640 B2 | 8/2006 | Wang et al. |
| 7,139,601 B2 | 11/2006 | Bucholz et al. |
| 7,155,316 B2 | 12/2006 | Sutherland et al. |
| 7,158,736 B2 | 1/2007 | Sato et al. |
| 7,166,114 B2 | 1/2007 | Moctezuma De La Barrera et al. |
| 7,181,315 B2 | 2/2007 | Watanabe et al. |
| 7,204,844 B2 | 4/2007 | Jensen et al. |
| 7,206,626 B2 | 4/2007 | Quaid, III |
| 7,206,627 B2 | 4/2007 | Abovitz et al. |
| 7,215,326 B2 | 5/2007 | Rosenberg |
| 7,239,940 B2 | 7/2007 | Wang et al. |
| 7,249,951 B2 | 7/2007 | Bevirt et al. |
| 7,346,417 B2 | 3/2008 | Luth et al. |
| 7,404,716 B2 | 7/2008 | Gregorio et al. |
| 7,454,268 B2 | 11/2008 | Jinno |
| 7,466,303 B2 | 12/2008 | Yi et al. |
| 7,468,594 B2 | 12/2008 | Svensson et al. |
| 7,492,930 B2 | 2/2009 | Leitner et al. |
| 7,543,588 B2 | 6/2009 | Wang et al. |
| 7,561,733 B2 | 7/2009 | Vilsmeier et al. |
| 7,573,461 B2 | 8/2009 | Rosenberg |
| 7,625,383 B2 | 12/2009 | Charles et al. |
| 7,630,753 B2 | 12/2009 | Simon et al. |
| 7,648,513 B2 | 1/2010 | Green et al. |
| 7,660,623 B2 | 2/2010 | Hunter et al. |
| 7,683,565 B2 | 3/2010 | Quaid et al. |
| 7,725,162 B2 | 5/2010 | Malackowski et al. |
| 7,726,564 B2 | 6/2010 | Goldbach |
| 7,744,608 B2 | 6/2010 | Lee et al. |
| 7,747,311 B2 | 6/2010 | Quaid, III |
| 7,747,312 B2 | 6/2010 | Barrick et al. |
| 7,772,541 B2 | 8/2010 | Froggatt et al. |
| 7,801,342 B2 | 9/2010 | Boese et al. |
| 7,813,838 B2 | 10/2010 | Sommer |
| 7,818,044 B2 | 10/2010 | Dukesherer et al. |
| 7,824,424 B2 | 11/2010 | Jensen et al. |
| 7,831,292 B2 | 11/2010 | Quaid et al. |
| 7,835,784 B2 | 11/2010 | Mire et al. |
| 7,840,253 B2 | 11/2010 | Tremblay et al. |
| 7,892,243 B2 | 2/2011 | Stuart |
| 7,914,522 B2 | 3/2011 | Morley et al. |
| 7,950,306 B2 | 5/2011 | Stuart |
| 7,967,742 B2 | 6/2011 | Hoeg et al. |
| 7,987,001 B2 | 7/2011 | Teichman et al. |
| 8,010,180 B2 | 8/2011 | Quaid et al. |
| 8,027,526 B2 | 9/2011 | Boese et al. |
| 8,041,459 B2 | 10/2011 | Sutherland et al. |
| 8,187,180 B2 | 5/2012 | Pacey |
| 8,287,522 B2 | 10/2012 | Moses et al. |
| 8,320,612 B2 | 11/2012 | Knobel et al. |
| 8,343,048 B2 | 1/2013 | Warren, Jr. |

(56) References Cited

U.S. PATENT DOCUMENTS

| | | |
|---|---|---|
| 8,382,372 B2 | 2/2013 | Maschke |
| 8,442,621 B2 | 5/2013 | Gorek et al. |
| 8,792,963 B2 | 7/2014 | Zhao et al. |
| 8,838,205 B2 | 9/2014 | Shoham et al. |
| 8,945,140 B2 | 2/2015 | Hubschman et al. |
| 8,954,132 B2 | 2/2015 | Hubschman et al. |
| 8,974,380 B2 | 3/2015 | Michaeli et al. |
| 9,002,432 B2 | 4/2015 | Feilkas |
| 9,008,757 B2 | 4/2015 | Wu |
| 9,044,257 B2 | 6/2015 | Fielding et al. |
| 9,119,638 B2 | 9/2015 | Schwarz et al. |
| 9,119,655 B2 | 9/2015 | Bowling et al. |
| 9,119,670 B2 | 9/2015 | Yang et al. |
| 9,168,104 B2 | 10/2015 | Dein |
| 9,188,973 B2 | 11/2015 | Tenney et al. |
| 9,283,048 B2 | 3/2016 | Kostrzewski et al. |
| 9,307,969 B2 | 4/2016 | Novak et al. |
| 9,381,085 B2 | 7/2016 | Axelson, Jr. et al. |
| 9,402,691 B2 | 8/2016 | Merritt et al. |
| 9,420,944 B2 | 8/2016 | Sutherland et al. |
| 9,480,534 B2 | 11/2016 | Bowling et al. |
| 9,492,240 B2 | 11/2016 | Itkowitz et al. |
| 9,510,771 B1 | 12/2016 | Finley et al. |
| 9,510,914 B2 | 12/2016 | Yang et al. |
| 9,542,743 B2 | 1/2017 | Tenney et al. |
| 9,566,052 B2 | 2/2017 | Novak |
| 9,566,120 B2 | 2/2017 | Malackowski et al. |
| 9,603,665 B2 | 3/2017 | Bowling et al. |
| 9,615,987 B2 | 4/2017 | Worm et al. |
| 9,629,595 B2 | 4/2017 | Walker et al. |
| 9,642,606 B2 | 5/2017 | Charles et al. |
| 9,668,819 B2 | 6/2017 | Stolka et al. |
| 9,681,796 B2 | 6/2017 | Tesar et al. |
| 9,707,043 B2 | 7/2017 | Bozung |
| 9,718,190 B2 | 8/2017 | Larkin et al. |
| 9,733,336 B2 | 8/2017 | Shen et al. |
| 9,733,463 B2 | 8/2017 | Eslami et al. |
| RE46,562 E | 10/2017 | Huennekens et al. |
| 9,833,254 B1 | 12/2017 | Barral et al. |
| 9,867,531 B2 | 1/2018 | Pacey et al. |
| 9,901,408 B2 | 2/2018 | Larkin |
| 9,901,409 B2 | 2/2018 | Yang et al. |
| 9,933,606 B2 | 4/2018 | Saur et al. |
| 9,987,093 B2 | 6/2018 | Christian et al. |
| 10,039,474 B2 | 8/2018 | Taylor et al. |
| 10,045,882 B2 | 8/2018 | Balicki et al. |
| 10,064,691 B2 | 9/2018 | Frimer et al. |
| 10,154,882 B2 | 12/2018 | Garbey et al. |
| 10,159,532 B1 | 12/2018 | Ummalaneni |
| 10,165,981 B2 | 1/2019 | Schoepp |
| 10,178,368 B2 | 1/2019 | Zhao et al. |
| 10,247,545 B2 | 4/2019 | Elliot |
| 10,512,509 B2 | 12/2019 | Bowling et al. |
| 10,531,926 B2 | 1/2020 | Roessler |
| 10,667,868 B2 | 6/2020 | Malackowski |
| 11,266,465 B2 | 3/2022 | Panescu et al. |
| 11,517,377 B2 | 12/2022 | Malackowski et al. |
| 2002/0035321 A1 | 3/2002 | Bucholz et al. |
| 2002/0120188 A1 | 8/2002 | Brock et al. |
| 2003/0078470 A1 | 4/2003 | Borst et al. |
| 2003/0125622 A1 | 7/2003 | Schweikard et al. |
| 2003/0181800 A1 | 9/2003 | Bonutti |
| 2003/0208296 A1 | 11/2003 | Brisson et al. |
| 2004/0010190 A1 | 1/2004 | Shahidi |
| 2004/0024311 A1 | 2/2004 | Quaid |
| 2004/0034283 A1 | 2/2004 | Quaid |
| 2004/0034302 A1 | 2/2004 | Abovitz et al. |
| 2004/0059194 A1 | 3/2004 | Berg et al. |
| 2004/0073279 A1 | 4/2004 | Malackowski et al. |
| 2004/0077939 A1 | 4/2004 | Graumann |
| 2004/0106916 A1 | 6/2004 | Quaid et al. |
| 2004/0138556 A1 | 7/2004 | Cosman |
| 2005/0054895 A1 | 3/2005 | Hoeg et al. |
| 2005/0054897 A1 | 3/2005 | Hashimoto et al. |
| 2005/0143651 A1 | 6/2005 | Verard et al. |
| 2005/0171553 A1 | 8/2005 | Schwarz et al. |
| 2005/0203490 A1 | 9/2005 | Simonson |
| 2006/0020279 A1 | 1/2006 | Chauhan et al. |
| 2006/0109266 A1 | 5/2006 | Itkowitz et al. |
| 2006/0142657 A1 | 6/2006 | Quaid et al. |
| 2006/0155262 A1 | 7/2006 | Kishi et al. |
| 2006/0176242 A1 | 8/2006 | Jaramaz et al. |
| 2006/0258938 A1 | 11/2006 | Hoffman et al. |
| 2007/0135686 A1 | 6/2007 | Pruitt et al. |
| 2007/0183637 A1 | 8/2007 | Kreuzer et al. |
| 2007/0260394 A1 | 11/2007 | Dean |
| 2007/0265527 A1 | 11/2007 | Wohlgemuth |
| 2007/0270685 A1 | 11/2007 | Kang et al. |
| 2007/0287911 A1 | 12/2007 | Haid et al. |
| 2008/0021283 A1 | 1/2008 | Kuranda |
| 2008/0058776 A1 | 3/2008 | Jo et al. |
| 2008/0077158 A1 | 3/2008 | Haider et al. |
| 2008/0108912 A1 | 5/2008 | Node-Langlois |
| 2008/0161829 A1 | 7/2008 | Kang |
| 2008/0183068 A1 | 7/2008 | Carls et al. |
| 2008/0200794 A1 | 8/2008 | Teichman et al. |
| 2008/0212082 A1 | 9/2008 | Froggatt et al. |
| 2008/0214898 A1 | 9/2008 | Warren |
| 2008/0243142 A1 | 10/2008 | Gildenberg |
| 2008/0281989 A1 | 11/2008 | Hager et al. |
| 2009/0003975 A1 | 1/2009 | Kuduvalli et al. |
| 2009/0024140 A1 | 1/2009 | Allen et al. |
| 2009/0157059 A1 | 6/2009 | Allen et al. |
| 2010/0295931 A1 | 11/2010 | Schmidt |
| 2010/0331859 A1 | 12/2010 | Omori |
| 2011/0075912 A1 | 3/2011 | Rieber et al. |
| 2011/0106102 A1 | 5/2011 | Balicki et al. |
| 2011/0130761 A1 | 6/2011 | Plaskos et al. |
| 2011/0152676 A1 | 6/2011 | Groszmann et al. |
| 2011/0263971 A1 | 10/2011 | Nikou et al. |
| 2011/0264107 A1 | 10/2011 | Nikou et al. |
| 2012/0059378 A1 | 3/2012 | Farrell |
| 2012/0071752 A1 | 3/2012 | Sewell et al. |
| 2012/0071893 A1 | 3/2012 | Smith et al. |
| 2012/0143084 A1 | 6/2012 | Shoham |
| 2012/0190965 A1 | 7/2012 | Schaerer et al. |
| 2012/0330429 A1 | 12/2012 | Axelson, Jr. et al. |
| 2013/0006267 A1 | 1/2013 | Odermatt et al. |
| 2013/0019883 A1 | 1/2013 | Worm et al. |
| 2013/0060278 A1 | 3/2013 | Bozung et al. |
| 2013/0096574 A1 | 4/2013 | Kang et al. |
| 2013/0169423 A1 | 7/2013 | Iorgulescu et al. |
| 2014/0005684 A1 | 1/2014 | Kim et al. |
| 2014/0031668 A1 | 1/2014 | Mobasser et al. |
| 2014/0039681 A1 | 2/2014 | Bowling et al. |
| 2014/0107426 A1 | 4/2014 | Wilson |
| 2014/0171787 A1 | 6/2014 | Garbey et al. |
| 2014/0180290 A1 | 6/2014 | Otto et al. |
| 2014/0200621 A1 | 7/2014 | Malackowski et al. |
| 2014/0221822 A1 | 8/2014 | Ehlers et al. |
| 2014/0276943 A1 | 9/2014 | Bowling et al. |
| 2015/0005643 A1 | 1/2015 | Whitman et al. |
| 2015/0018622 A1 | 1/2015 | Tesar et al. |
| 2015/0265370 A1 | 9/2015 | Garbey et al. |
| 2015/0351860 A1 | 12/2015 | Piron et al. |
| 2016/0113728 A1 | 4/2016 | Piron et al. |
| 2016/0183911 A1 | 6/2016 | Waksman |
| 2016/0191887 A1* | 6/2016 | Casas .................... A61B 34/10 348/47 |
| 2016/0242858 A1 | 8/2016 | Moctezuma de la Barrera et al. |
| 2016/0278864 A1 | 9/2016 | Paitel |
| 2016/0345917 A1 | 12/2016 | Daon et al. |
| 2017/0018925 A1 | 1/2017 | Emby |
| 2017/0143429 A1 | 5/2017 | Richmond et al. |
| 2017/0143432 A1 | 5/2017 | Bowling et al. |
| 2017/0189125 A1 | 7/2017 | Malackowski |
| 2017/0209225 A1 | 7/2017 | Wu |
| 2017/0215857 A1 | 8/2017 | D'Urso |
| 2017/0238998 A1 | 8/2017 | Srimohanarajah et al. |
| 2017/0265947 A1 | 9/2017 | Dyer et al. |
| 2017/0281282 A1 | 10/2017 | Noonan et al. |
| 2017/0296162 A1 | 10/2017 | Wan |
| 2017/0312036 A1 | 11/2017 | Hoffman et al. |
| 2017/0325674 A1 | 11/2017 | Kleiner et al. |

(56) References Cited

U.S. PATENT DOCUMENTS

| | | | |
|---|---|---|---|
| 2017/0333137 A1* | 11/2017 | Roessler | A61B 17/1703 |
| 2017/0358091 A1 | 12/2017 | Ekin | |
| 2018/0078315 A1 | 3/2018 | Ren et al. | |
| 2018/0116732 A1 | 5/2018 | Lin et al. | |
| 2018/0147727 A1 | 5/2018 | Mewes et al. | |
| 2018/0153626 A1 | 6/2018 | Yang et al. | |
| 2018/0199951 A1 | 7/2018 | Chappuis et al. | |
| 2018/0228553 A1 | 8/2018 | Bai et al. | |
| 2018/0235715 A1 | 8/2018 | Amiot et al. | |
| 2018/0303580 A1 | 10/2018 | Salah et al. | |
| 2018/0311012 A1 | 11/2018 | Moctezuma et al. | |
| 2018/0368929 A1 | 12/2018 | Popovic et al. | |
| 2019/0050984 A1 | 2/2019 | Blendinger | |
| 2019/0059833 A1 | 2/2019 | Govari | |
| 2019/0069962 A1 | 3/2019 | Tabandeh et al. | |
| 2019/0328479 A1 | 10/2019 | Wada et al. | |
| 2020/0030046 A1 | 1/2020 | Bowling et al. | |
| 2020/0085513 A1 | 3/2020 | Bowling et al. | |
| 2020/0100849 A1 | 4/2020 | Malackowski et al. | |
| 2020/0281663 A1 | 9/2020 | Malackowski | |
| 2021/0153918 A1 | 5/2021 | Moctezuma de la Barrera et al. | |
| 2021/0338341 A1 | 11/2021 | Malackowski | |

FOREIGN PATENT DOCUMENTS

| | | |
|---|---|---|
| CN | 106096559 A | 11/2016 |
| CN | 106127788 A | 11/2016 |
| CN | 107714175 A | 2/2018 |
| CN | 109272481 A | 1/2019 |
| CN | 109708655 A | 5/2019 |
| DE | 19639615 C2 | 10/1999 |
| EP | 0685088 B1 | 9/2000 |
| EP | 1321105 B1 | 8/2003 |
| EP | 1545368 B1 | 3/2009 |
| EP | 3449859 A1 | 3/2019 |
| JP | 2005532890 A | 11/2005 |
| JP | 2006106419 A | 4/2006 |
| JP | 2018506352 A | 3/2018 |
| KR | 20100098055 A | 9/2010 |
| KR | 20110036453 A | 4/2011 |
| KR | 20160138142 A | 12/2016 |
| WO | 9611624 A2 | 4/1996 |
| WO | 99037220 A1 | 7/1999 |
| WO | 0021450 A1 | 4/2000 |
| WO | 0035366 A1 | 6/2000 |
| WO | 0059397 A1 | 10/2000 |
| WO | 0060571 A1 | 10/2000 |
| WO | 0103586 A1 | 1/2001 |
| WO | 0139683 A1 | 6/2001 |
| WO | 0200131 A1 | 1/2002 |
| WO | 0224051 A2 | 3/2002 |
| WO | 02060653 A2 | 8/2002 |
| WO | 02065931 A1 | 8/2002 |
| WO | 02074500 A2 | 9/2002 |
| WO | 02076302 A2 | 10/2002 |
| WO | 03094108 A2 | 11/2003 |
| WO | 2004001569 A2 | 12/2003 |
| WO | 2004014244 A2 | 2/2004 |
| WO | 2004019785 A2 | 3/2004 |
| WO | 2004069036 A2 | 8/2004 |
| WO | 2005009215 A2 | 2/2005 |
| WO | 2006058633 A1 | 6/2006 |
| WO | 2006063156 A1 | 6/2006 |
| WO | 2006091494 A1 | 8/2006 |
| WO | 2006106419 A2 | 10/2006 |
| WO | 2007017642 A1 | 2/2007 |
| WO | 2007111749 A2 | 10/2007 |
| WO | 2007117297 A2 | 10/2007 |
| WO | 2007136739 A2 | 11/2007 |
| WO | 2007136768 A2 | 11/2007 |
| WO | 2007136769 A2 | 11/2007 |
| WO | 2007136771 A2 | 11/2007 |
| WO | 2009045827 A2 | 4/2009 |
| WO | 2009059330 A2 | 5/2009 |
| WO | 2009131716 A1 | 10/2009 |
| WO | 2011021192 A1 | 2/2011 |
| WO | 2011088541 A1 | 7/2011 |
| WO | 2011106861 A1 | 9/2011 |
| WO | 2011113483 A1 | 9/2011 |
| WO | 2011128766 A2 | 10/2011 |
| WO | 2011133873 A1 | 10/2011 |
| WO | 2011133927 A2 | 10/2011 |
| WO | 2011134083 A1 | 11/2011 |
| WO | 2012018816 A2 | 2/2012 |
| WO | 2013132501 A1 | 9/2013 |
| WO | 2015087218 A1 | 6/2015 |
| WO | 2015100310 A1 | 7/2015 |
| WO | 2017012624 A1 | 1/2017 |
| WO | 2017059870 A1 | 4/2017 |
| WO | 2017158592 A2 | 9/2017 |
| WO | 2017187795 A1 | 11/2017 |
| WO | 2017195192 A1 | 11/2017 |
| WO | 2017205351 A1 | 11/2017 |
| WO | 2018237187 A2 | 12/2018 |
| WO | 2018237187 A3 | 1/2019 |
| WO | 2019070729 A1 | 4/2019 |
| WO | 2019070997 A1 | 4/2019 |

OTHER PUBLICATIONS

Fadda, M. et al., "Premiers Pas Vers La Dissectomie et la Realisation de Protheses du Genou a L'Aide de Robots", Innov. Tech. Bio. Med. , 1992, pp. 394-409, vol. 13, No. 4; 16 pages.

Fluete, M. et al., "Incorporating a statistically based shape model into a system for computer-assisted anterior cruciate ligament surgery", Medical Image Analysis, Oct. 1999, pp. 209-222, vol. 3, No. 3, FR; 14 pages.

Grueneis, C.O.R et al., "Clinical Introduction of the Caspar System Problems and Initial Results", 4th International Symposium of Computer Assited Orthopaedic Surgery, CAOS'99, Abstracts from CAOS '99, 1999, p. 160, Davos, Switzerland; 1 pages.

Haider, H. et al., Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.

Harris, S.J. et al., "Experiences with Robotic Systems for Knee Surgery", CVRMed-MRCAS'97, Lecture Notes in Computer Science, 1997, pp. 757-766, vol. 1205, Springer Berlin Heidelberg,London, UK; 10 pages.

Harris,S.J. et al., "Intra-operative Application of a Robotic Knee Surgery System", Medical Image Computing and Computer-Assisted Intervention—MICCAI'99, 1999, pp. 1116-1124, vol. 1679, Springer-Verlag Berlin Heidelberg; 9pages.

Hassfeld, S. et al., "Intraoperative Navigation Techniques Accuracy Tests and Clinical Report", In: Computer Assisted Radiology and Surgery (CARS'98), Tokyo, Jun. 1998, pp. 670-675, Elseview Science B.V.; 6 pages.

Ho, S.C. et al., "Force Control for Robotic Surgery", ICAR '95, 1995, pp. 21-32, London, UK; 12 pages.

Ho, S.C. et al., "Robot Assisted Knee Surgery", IEEE Engineering in Medicine and Biology, May/Jun. 1995, pp. 292-300, vol. 14, No. 3; 9 pages.

Hyosig, K. et al., "Autonomous Suturing using Minimally Invasive Surgical Robots", Control Applications, Sep. 25-27, 2000. Proceedings of the 2000 IEEE International Conference on, 2000, pp. 742-747, IEEE, Anchorage, AK, USA, 6 pages.

Hyosig, K. et al., "EndoBot A Robotic Assistant in Minimally Invasive Surgeries", Robotics and Automation, 2001. Proceedings 2001 ICRA. IEEE International Conference on, Seoul, KR, 2001, pp. 2031-2036, vol. 2, IEEE, Troy, NY, USA; 6 pages.

International Search Report for Application No. PCT/US2014/024269 dated Oct. 17, 2014, 6 pages.

International Search Report for Application No. PCT/US2016/069152 dated Apr. 6, 2017, 2 pages.

International Search Report for Application No. PCT/US2020/040717 dated Oct. 7, 2020, 3 pages.

Jakopec, M. et al., "The first clinical application of a "hands-on" robotic knee surgery system", Computer Aided Surgery , 2001, pp. 329-339, vol. 6, Issue 6, Wiley-Liss, Inc.; 11 pages.

(56) References Cited

OTHER PUBLICATIONS

Jaramaz, B. et al., "Range of Motion After Total Hip Arthroplasty Experimental Verification of the Analytical Simulator", CVRMed-MRCAS'97, Lecture Notes in Computer Science, Feb. 20, 1997, pp. 573-582, vol. 1205,Springer Berlin Heidelberg, Pittsburgh, PA, USA; 14 pages.
Kato A., et al., "A frameless, armless navigational system for computer-assisted neurosurgery", Technical note, Journal of Neurosurgery, vol. 74, May 1991, pp. 845-849; 5 pages.
Kazanzides, P. et al., "Architecture of a Surgical Robot", Systems, Man and Cybernetics, 1992., IEEE International Conference on, Oct. 18-21, 1992, pp. 1624-1629, vol. 2, IEEE, Chicago, IL, USA; 6 pages.
Khadem, R. et al., "Comparative Tracking Error Analysis of Five Different Optical Tracking Systems", Computer Aided Surgery, 2000, pp. 98-107, vol. 5, Stanford, CA, USA; 10 pages.
Kienzle, T.C. et al., "An Integrated CAD-Robotics System for Total Knee Replacement Surgery", Systems, Man and Cybernetics, 1992., IEEE International Conference on, Oct. 18-21, 1992, pp. 1609-1614, vol. 2,IEEE, Chicago, IL, USA; 6 pages.
Kienzle, T.C. et al., "Total Knee Replacement Computer-assisted surgical system uses a calibrated robot", Engineering in Medicine and Biology, May 1995, pp. 301-306, vol. 14, Issue 3,IEEE; 35 pages.
Koseki, Y. et al., "Robotic assist for MR-guided surgery using leverage and parallelepiped mechanism", Medical Image Computing and Computer-Assisted Intervention—MICCAI 2000, Lecture Notes in Computer Science, 2000, pp. 940-948, vol. 1935, Springer Berlin Heidelberg; 9 pages.
Lavallee, S. et al., "Computer Assisted Spine Surgery a technique for accurate transpedicular screw fixation using CT data and a 3-D optical localizer", Journal of Image Guided Surgery, 1995, pp. 65-73; 9 pages.
Lea, J.T. et al., "Registration and immobilization in robot-assisted surgery", Journal of Image Guided Surgery, Computer Aided Surgery, 1995, vol. 1, No. 2, pp. 80-87; 11 pages.
Lea, J.T. Registration Graphs a Language for Modeling and Analyzing Registration in Image-Guided Surgery, Dec. 1998, Evanston, Illinois, US; 49 pages.
Leitner, F. et al., "Computer-Assisted Knee Surgical Total Replacement", CVRMed-MRCAS'97, Lecture Notes in Computer Science vol. 1205, 1997, pp. 629-638, Springer Berlin Heidelberg, Jan. 1, 1997; 10 pages.
Levison, T.J. et al., "Surgical Navigation for THR a Report on Clinical Trial Utilizing HipNav", MICCAI 2000, LNCS 1935, pp. 1185-1187, 2000, Springer-Verlag Berlin Heidelberg; 3 pages.
Louhisalmi, Y. et al., "Development of a Robotic Surgical Assistant", 1994, pp. 1043-1044, IEEE, Linnanmaa, Oulu, FI; 2 pages.
Matsen, F.A. et al., Robotic Assistance in Orthopaedic Surgery a Proof of Principle Using Distal Femoral Arthroplasty, Clinical Orthopaedic Related Research, Nov. 1993, pp. 178-186, vol. 296; 9 pages.
Meng, C. et al., "Remote surgery case robot-assisted teleneurosurgery", Robotics and Automation, 2004. Proceedings. ICRA '04. 2004 IEEE International Conference on, Apr. 26-May 1, 2004, pp. 819-823, vol. 1, IEEE,New Orleans, LA, USA; 5 pages.
Moctezuma, J. L. et al., "A Computer and Robotic Aided Surgery System for Accomplishing Osteotomies", First International Symposium onMedical Robotics and Computer Assisted Surgery, Sep. 22-24, 1994, Pittsburgh, Pennsylvania, US; 6 pages.
Nolte, L.P. et al., "A Novel Approach to Computer Assisted Spine Surgery", Proc. First International Symposium on Medical Robotics and Computer Assisted Surgery, Pittsburgh, 1994, pp. 323-328; 7 pages.
O'Toole, R.V. et al., "Biomechanics for Preoperative Planning and Surgical Simulations in Orthopaedics", Computers in Biology and Medicine, Mar. 1995, pp. 183-191, vol. 25, Issue 2; 8 pages.
Orto Maquet and Caspar: An Automated Cell for Prosthesis Surgery, Robotics World, Sep./Oct. 1999, pp. 30-31, Circular No. 87 on Reader Reply Card; 2 pages.
Park, Shinsuk, "Safety Strategies for Human-Robot Interaction in Surgical Environment," SICE-ICASE, 2006. International Joint Conference, Oct. 18-21, 2006, pp. 1769-1773, IEEE, Bexco, Busan, SK; 5 pages.
Paul, H.A. et al., A Surgical Robot for Total Hip Replacement Surgery, International Conference on Robotics and Automation, 1992, pp. 606-611, IEEE,Nice, FR; 6 pages.
Paul, H.A. et al., "Development of a Surgical Robot for Cementless Total Hip Arthroplasty", Clinical Orthopaedics and Related Research, Dec. 1992, pp. 57-66, No. 285, Sacramento, CA, USA; 10 pages.
Paul, H.A.et al., "Robotic Execution of a Surgical Plan, Systems, Man and Cybernetics", 1992., IEEE International Conference on, Oct. 18-21, 1992,pp. 1621-1623, IEEE, Sacramento, California, US; 3 pages.
Preising, B. et al. "A Literature Review Robots in Medicine", Engineering in Medicine and Biology Magazine, IEEE (vol. 10, Issue: 2), Jun. 1991, pp. 13-22, IEEE; 10 pages.
Quaid, A.E. et al., "Haptic Information Displays for Computer-Assisted Surgery", Robotics and Automation, 2002 Proceedings. ICRA '02. IEEE International Conference on, May 2002, pp. 2092-2097, vol. 2, IEEE, Washington DC, USA; 6 pages.
Raczkowsky, J. et al., "Ein Robotersystem fur craniomaxillofaciale chirurgische Eingriffe (A robotic system for surgical procedures craniomaxillofaciale)", with English language abstract, Computer Forsch. Entw., 1999, pp. 24-35, vol. 14,Springer-Verlag; 12 pages.
Rembold, U. et al., "Surgical Robotics: An Introduction", Journal of Intelligent and Robotic Systems vol. 30, No. 1, pp. 1-28, 2001, Kluwer Academic Publishers; 28 pages.
Riviere, C.N. et al., "Modeling and Canceling Tremor in Human-Machine Interfaces", Engineering in Medicine and Biology Magazine, IEEE, vol. 15, Issue 3, May/Jun. 1996, pp. 29-36, IEEE; 8 pages.
Rohling, R.et al., "Comparison of Relative Accuracy Between a Mechanical and an Optical Position Tracker for Image-Guided Neurosurgery", Journal of Image Guided Surgery, 1995, pp. 30-34, vol. 1, No. 1; 4 pages.
Salisbury, J.K., Active Stiffness Control of a Manipulator in Cartesian Coordinates, Decision and Control including the Symposium on Adaptive Processes, 1980 19th IEEE Conference on, Dec. 1980, pp. 95-100, vol. 19, IEEE, Stanford, CA, USA; 7 pages.
Santos, Julio J. et al., "A Stereotactic/Robotic System for Pedicle Screw Placement", Interactive Technology and the New Paradigm for Healthcare, (Proceedings of theMedicine Meets Virtual Reality III Conference, San Diego, 1995), pp. 326-333, IOS Press and Ohmsha; 8 pages.
Schmidt, T. et al., "EasyGuide Neuro, A New System for Image-Guided Planning", Simulation and Navigation in Neurosurgery, Biomedical Engineering, vol. 40, Supplement 1, 1995, pp. 233-234, Hamburg, DE; 2 pages, and partial English language translation of EasyGuide Neuro, A New System for Image-Guided Planning, Simulation and Navigation in Neurosurgery, 1 page.
Seibold, B. et al., "Prototype of Instrument for Minimally Invasive Surgery with 6-Axis Force Sensing Capabilit", Robotics and Automation, 2005. ICRA 2005. Proceedings of the 2005 IEEE International Conference on, Apr. 18-22, 2005, pp. 498-503, IEEE, Barcelona, Spain; 6 pages.
Shinsuk, P., Safety Strategies for Human-Robot Interaction in Surgical Environment, SICE-ICASE, 2006. International Joint Conference, Oct. 18-21, 2006, pp. 1769-1773, IEEE, Bexco, Busan, SK; 5 pages.
Siebert W. et al., "Technique and first clinical results of robot-assisted total knee replacement", The Knee, Sep. 2002, pp. 173-180, vol. 9, Issue 3, Elsevier B.V.; 8 pages.
Abovitz, R., "Digital surgery the future of medicine and human-robot symbiotic interaction", Industrial Robot: An International Journal, 2001, pp. 401-406, vol. 28, Issue 5, Hollywood, FL, USA; 5 pages.
Abovitz, R.A., "Human-Interactive Medical Robotics", Abstract for CAOS 2000, 2000, pp. 71-72; 2 pages.
Ansara, D. et al., "Visual and haptic collaborative tele-presence", Computers & Graphics, 2001, vol. 25, Elsevier, Inc., pp. 789-798.

(56) References Cited

OTHER PUBLICATIONS

Baerentzen, J. Andreas, "Octree-based Volume Sculpting", Proc. Late Breaking Hot Topics, IEEE Visualization '98, pp. 9-12, 1998; 4 pages.

Bainville, E. et al., "Concepts and Methods of Registration for Computer-Integrated Surgery", Computer Assisted Orthopedic Surgery (CAOS), 1999, pp. 15-34, Hogrefe & Huber Publishers, Bern; 22 pages.

Bargar, W.L. et al., "Primary and Revision Total Hip Replacement Using the Robodoc System", Clinical Orthopaedics and Related Research, Sep. 1998, pp. 82-91, No. 354; 10 pages.

Bouazza-Marouf, K. et al., "Robot-assisted invasive orthopaedic surgery", Mechatronics in Surgery, Jun. 1996, pp. 381-397, vol. 6, Issue 4, UK; 17 pages.

Brandt, G. et al., "CRIGOS: A Compact Robot for Image-Guided Orthopedic Surgery," Information Technology in Biomedicine, IEEE Transactions on, vol. 3, No. 4, pp. 252-260, Dec. 1999; 9 pages.

Brisson, G. et al., Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-Verlag Berlin Heidelberg 2004; 8 pages.

Buckingham, R.O., "Robotics in surgery a new generation of surgical tools incorporate computer technology and mechanical actuation to give surgeons much finer control than previously possible during some operations", IEE Review, Sep. 1994, pp. 193-196; 4 pages.

Buckingham, R.O., "Safe Active Robotic Devices for Surgery", Systems, Man and Cybernetics, 1993. 'Systems Engineering in the Service of Humans', Conference Proceedings., International Conference on, Oct. 17-20, 1993, pp. 355-358, vol. 5, IEEE, LeTougeut; 4 pages.

Burghart, C. et al., "Robot Controlled Osteotomy in Craniofacial Surgery", First International Workshop on Haptic Devices in Medical Applications Proceedings, Jun. 23, 1999, pp. 12-22, Paris, FR; 13 pages.

Burghart, C.R. et al., "Robot assisted craniofacial surgery first clinical evaluation", Computer Assisted Radiology and Surgery, 1999, pp. 828-833; 7 pages.

Burghart, C.R., "Robotergestutzte Osteotomie in der craniofacialen Chirurgie (Robot Clipped osteotomy in craniofacial surgery)", Jul. 1, 1999, GCA-Verlag, 2000; 250 pages.

Choi, D. et al., "Flexure-based Manipulator for Active Handheld Microsurgical Instrument", Engineering in Medicine and Biology Society, 2005. Proceedings of the 2005 IEEE Engineering in Medicine and Biology 27th Annual Conference of theDigital Object Identifier, 2005, pp. 5085-5088, IEEE, Shanghai, China, Sep. 1-4, 2005; 4 pages.

Colgate, J.E. et al., "Issues in the Haptic Display of Tool Use", Intelligent Robots and Systems 95. 'Human Robot Interaction and Cooperative Robots', Proceedings. 1995 IEEE/RSJ International Conference on, Aug. 5-9, 1995, pp. 140-145, vol. 3, IEEE, Pittsburgh, PA, USA; 6 pages.

Davies, B,L., "Computer-assisted and robotics surgery", International Congress and Symposium Series 223, 1997, pp. 71-82, Royal Society of Medicine Press Limited; 12 pages.

Davies, B.. "A review of robotics in surgery", Proceedings of the Institution of Mechanical Engineers, Part H: Journal of Engineering in Medicine Jan. 1, 2000, vol. 214, No. 1, pp. 129-140, Sage Publications; 13 pages.

Davies, B.L. et al., "Acrobot—using robots and surgeons synergistically in knee surgery", Advanced Robotics, 1997. ICAR '97. Proceedings., 8th International Conference on, Jul. 7-9, 1997, pp. 173-178, IEEE, Monterey, CA, USA; 6 pages.

Davies, B.L. et al., "Active compliance in robotic surgery—the use of force control as a dynamic constraint", Proceedings of the Institution of Mechanical Engineers, Part H: Journal of Engineeringin Medicine, Apr. 1, 1997, pp. 285-292, vol. 211, Sage; 9 pages.

Davies, B.L. et al., "Neurobot a special-purpose robot for neurosurgery", Robotics and Automation, 2000. Proceedings. ICRA '00. IEEE International Conference on, Apr. 2000, pp. 4103-4108, vol. 4, IEEE, San Francisco, CA, USA; 6 pages.

Davies, B.L., "Robotics in minimally invasive surgery", Through the Keyhole: Microengineering in Minimally Invasive Surgery, IEE Colloquium on, Jun. 6, 1995, p. 5/1-5/2, London, UK; 2 pages.

Delp, S.L. et al., "Computer Assisted Knee Replacement", Clinical Orthopaedics, Sep. 1998, pp. 49-56, vol. 354, Lippincott-Raven Publishers; 8 pages.

Digioia, A.M. et al., "Computer Assisted Orthopaedic Surgery Image Guided and Robotic Assistive Technologies, Clinical Orthopaedics & Related Research":. Sep. 1998, pp. 8-16, vol. 354, Lippincott Williams & Wilkins, Pittsburgh, PA, USA; 9 pages.

Doignon, C. et al., "Segmentation and guidance of multiple rigid objects for intra operative endoscopic vision", Proceeding WDV'05/WDV'06/ICCV'05/ECCV'06 Proceedings of the 2005/2006 International Conference on Dynamical Vision, 2006, pp. 314-327, Springer-Verlag Berlin, Heidelberg, Illkirch, FR; 14 pages.

Ellis, R.E. et al., "A surgical planning and guidance system for high tibial osteotomy", Computer Aided Surgery, Apr. 16, 1999, 264-274, vol. 4, Wiley-Liss, Inc.; 11 pages.

Engel, D. et al., "A Safe Robot System for Craniofacial Surgery", Robotics and Automation, 2001. Proceedings 2001 ICRA. IEEE International Conference on (vol. 2), pp. 2020-2024, IEEE; 5 pages.

English language abstract and machine-assisted English language translation for WO 00/21450 A1 extracted www.espacenet.com on Mar. 10, 2022, 9 pages.

English language abstract and machine-assisted English language translation for WO 00/59397 A1 extracted www.espacenet.com Mar. 10, 2022, 8 pages.

English language abstract and machine-assisted English translation for DE 196 39 615 C2 extracted from espacenet.com database on Mar. 10, 2022, 21 pages.

English language abstract and machine-assisted English translation for KR 2010-0098055 A extracted from espacenet.com database on Mar. 10, 2022, 9 pages.

English language abstract and machine-assisted English translation for KR 2011-0036453 A extracted from espacenet.com database on Mar. 10, 2022, 27 pages.

English language abstract and machine-assisted English translation for WO 02/074500 A2 extracted from espacenet.com database on Mar. 10, 2022, 10 pages.

English language abstract and machine-assisted English translation for WO 02/076302 A2 extracted from espacenet.com database on Mar. 10, 2022, 22 pages.

English language abstract and machine-assisted English translation for WO 2000/021450 A1 extracted from espacenet.com database on Jul. 3, 2014, 11 pages.

English language abstract and machine-assisted English translation for WO 2002/065931 A1 extracted from espacenet.com database on Aug. 11, 2014, 8 pages.

English language abstract and machine-assisted English translation for WO 2002/074500 A2 extracted from espacenet.com database on Aug. 11, 2014, 8 pages.

English language abstract for CN 101254103 A extracted from espacenet.com database on Mar. 10, 2022, 2 pages.

English language abstract for EP 1 321 105 B1 extracted from espacenet.com database on Mar. 10, 2022, 2 pages.

English language abstract for JP 2005-532890 A extracted from espacenet.com database on Mar. 10, 2022, 1 page.

English language abstract for JP 2006-106419 A extracted from espacenet.com database on Mar. 10, 2022, 1 page.

English language abstract for WO 02/065931 A1 extracted from espacenet.com database on Mar. 10, 2022, 2 pages.

English language abstract for WO 2002/076302 A2 extracted from espacenet.com database on Aug. 13, 2014, 2 pages.

English language abstract for WO 2004/019785 A2 extracted from espacenet.com database on Mar. 10, 2022, 2 pages.

English language abstract for WO 2006/058633 A1 extracted from espacenet.com database on Aug. 13, 2014, 2 pages.

English language abstract for WO 2006/058633 A1 extracted from espacenet.com database on Mar. 10, 2022, 2 pages.

English language abstract for WO 2017/187795 A1 extracted from espacenet.com database on Jan. 20, 2022, 2 pages.

(56) References Cited

OTHER PUBLICATIONS

English language abstract not found for EP 0 685 088 B1; however, see English language equivalent U.S. Pat. No. 6,715,836. Original document extracted from espacenet.com database on Mar. 10, 2022, 13 pages.

Fadda, M. et al., "Computer Assisted Planning for Total Knee Arthroplasty", 1997, pp. 619-628; 10 pages.

Fadda, M. et al., "Computer-Assisted Knee Arthroplasty at Rizzoli Institutes", First International Symposium on Medical Robotics and ComputerAssisted Surgery, Sep. 22-24, 1994, pp. 26-30, Pittsburgh, Pennsylvania, US; 6 pages.

Sim, C. et al., Image-Guided Manipulator Compliant Surgical Planning Methodology for Robotic Skull-Base Surgery, Medical Imaging and Augmented Reality, 2001. Proceedings. International Workshop on, Jun. 10-12, 2001, pp. 26-29, IEEE, Shatin, HK; 4 pages.

Simon, D. A. et al., "Accuracy validation in image-guided orthopaedic surgery", In Medical Robotics and Computer Assisted Surgery, 1995, pp. 185-192, Wiley; 8 pages.

Spencer, E.H., "The ROBODOC Clinical Trial a Robotic Assistant for Total Hip Arthroplasty", Orthopaedic Nursing, Jan.-Feb. 1996, pp. 9-14, vol. 15, Issue 1; 6 pages.

Spetzger, U. et al., "Frameless Neuronavigation in Modern Neurosurgery", Minimally Invasive Neurosurgery, Dec. 1995, pp. 163-166, vol. 38; 4 pages.

Taylor, R. et al., "A Steady-Hand Robotic System for Microsurgical Augementation", MICCA199: the Second International Conference on Medical ImageComputing and Computer-Assisted Intervention, Cambridge, England, Sep. 19-22, 1999. MICCA199 Submission #1361999, pp. 1031-1041, Springer-Verlag Berlin Heidelberg; 11 pages.

Taylor, R.H. et al. "An Image-directed Robotic System for Hip Replacement Surgery", Oct. 1990, pp. 111-116, vol. 8, No. 5; 7 pages.

Taylor, R.H. et al., An Image-Directed Robotic System for Precise Orthopaedic Surgery, Robotics and Automation, IEEE Transactions on,Jun. 1994, pp. 261-275, vol. 10, Issue 3, IEEE; 15 pages.

Taylor, R.H. et al., "A Model-Based Optimal Planning and Execution System with Active Sensing and Passive Manipulation for Augmentation of Human Precision in Computer-Integrated Surgery", Experimental Robotics II, The 2nd International Symposium, Lecture Notes in Control and Information Sciences, pp. 177-195, vol. 190, Springer Berlin Heidelberg, Toulouse, FR, Jun. 25-27, 1991; 19 pages.

Tonet, O. et al., "An Augmented Reality Navigation System for Computer Assisted Arthroscopic Surgery of the Knee," Medical Image Computing and Computer-AssistedIntervention—MICCAI 2000, Lecture Notes in Computer Science, 2000, pp. 1158-1162, vol. 1935, Springer Berlin Heidelberg; 5 pages.

Troccaz, J. et al., A passive arm with dynamic constraints a solution to safety problems in medical robotics, Systems, Man and Cybernetics, 1993. 'Systems Engineering in the Service of Humans', Conference Proceedings., InternationalConference on, Oct. 17-20, 1993, pp. 166-171, vol. 3, IEEE, Le Touquet, FR; 6 pages.

Troccaz, J. et al., "Semi-Active Guiding Systems in Surgery—A Two-DOF Prototype of the Passive Arm with Dynamic Constraints (PADyC)", Mechatronics, Jun. 1996, pp. 399-421, vol. 6, Issue 4, 1996, Elsevier Ltd., UK; 23 pages.

Troccaz, J. et al., Guiding systems for computer-assisted surgery introducing synergistic devices and discussing the different approaches, Medical Image Analysis, Jun. 1998, vol. 2, No. 2, pp. 101-119, Elsevier B.V.; 19 pages.

Van Ham, G. et al., "Accuracy study on the registration of the tibia by means of an intramedullary rod in robot-assisted total knee arthroplasty", PosterSession—Knee Arthroplasty-Valencia Foyer, 46th Annual Meeting, Orthopaedic Research Society, Mar. 12-15, 2000, Orlando, Florida, Jan. 1, 2010, p. 450; 1 pages.

Van Ham, G. et al., Machining and Accuracy Studies for a Tibial Knee Implant Using a Force-Controlled Robot, Computer Aided Surgery, Feb. 1998, pp. 123-133, vol. 3, Wiley-Liss, Inc., Heverlee BE; 11 pages.

Wang, T. et al., "A robotized surgeon assistant", Intelligent Robots and Systems '94. 'Advanced Robotic Systems and the Real World', IROS '94. Proceedings of the IEEE/RSJ/GI International Conference on, Sep. 12- 16, 1994, pp. 862-869, vol. 2, IEEE, Munich, Germany; 8 pages.

Watanabe, E. et al., "Three-Dimensional Digitizer (Neuronavigator)—New Equipment for Computed Tomography-Guided Stereotaxic Surgery", Surgical Neurology, Jun. 1987, pp. 543-547, vol. 27, Issue 6, ElsevierInc.; 5 pages.

Zilles, C.B. et al., "A Constraint-Based God-object Method for Haptic Display", Intelligent Robots and Systems 95. 'Human Robot Interaction and Cooperative Robots', Proceedings. 1995 IEEE/RSJ International Conference on , Aug. 5-9, 1995, pp. 146-151, vol. 3, IEEE, MIT, Cambridge, MA, USA; 6 pages.

English language abstract for KR 20160138142 A extracted from espacenet.com database on Aug. 26, 2024, 2 pages.

English language abstract and machine-assisted English translation for CN 103083089 A extracted from espacenet.com database on Jun. 13, 2025, 17 pages.

English language abstract and machine-assisted English translation for CN 106096559 A extracted from espacenet.com database on Jun. 13, 2025, 22 pages.

English language abstract and machine-assisted English translation for CN 106127788 A extracted from espacenet.com database on Jun. 13, 2025, 20 pages.

English language abstract and machine-assisted English translation for CN 107714175 A extracted from espacenet.com database on Jun. 13, 2025, 18 pages.

English language abstract and machine-assisted English translation for CN 109272481 A extracted from espacenet.com database on Jun. 13, 2025, 10 pages.

English language abstract and machine-assisted English translation for CN 109708655 A extracted from espacenet.com database on Jun. 13, 2025, 20 pages.

\* cited by examiner

FIG. 11
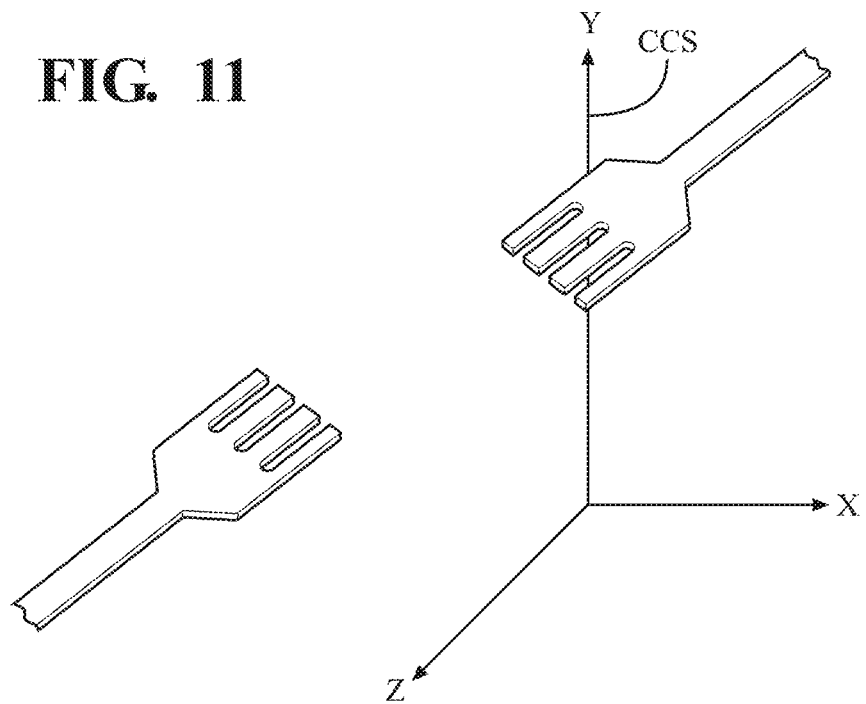
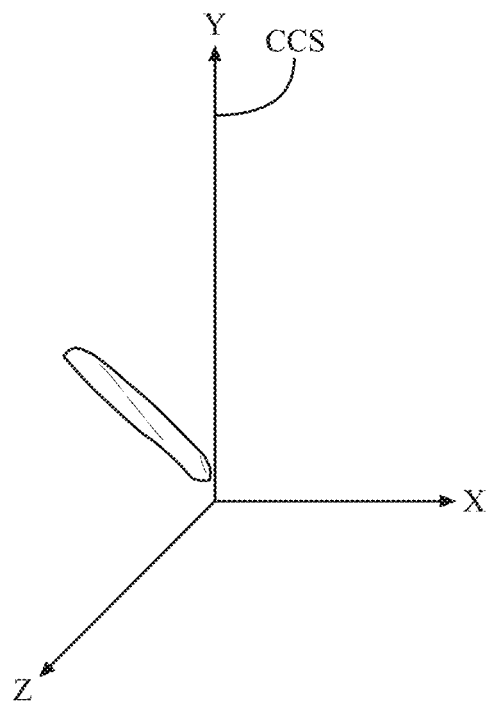
FIG. 12

OBSTACLE AVOIDANCE TECHNIQUES FOR SURGICAL NAVIGATION

CROSS-REFERENCE TO RELATED APPLICATIONS

The subject application is a bypass continuation of International Patent App. No. PCT/US2020/040717, filed on Jul. 2, 2020, which claims priority to and all the benefits of U.S. Provisional Patent App. No. 62/870,284, filed Jul. 3, 2019, the contents of each of the aforementioned applications being hereby incorporated by reference in their entirety.

TECHNICAL FIELD

The present disclosure generally relates to surgical navigation systems.

BACKGROUND

Surgical navigation systems assist in positioning surgical instruments relative to target volumes of patient tissue for treatment. During a surgical procedure, the target volume to be treated is frequently located adjacent sensitive anatomical structures and surgical tools that should be avoided. Tracking these adjacent anatomical structures using attached trackers is often difficult due to the flexible nature of the structures. Furthermore, attaching trackers to each object adjacent the target volume congests the surgical workspace and increases the cost and complexity of the surgical navigation system.

SUMMARY

In a first aspect, a navigation system is provided comprising: a localizer configured to detect a first object; a vision device configured to generate an actual depth map of surfaces near the first object; and a controller coupled to the localizer and the vision device, the controller configured to: access a virtual model corresponding to the first object; identify a positional relationship between the localizer and the vision device in a common coordinate system; generate an expected depth map of the vision device based on the detected position of the first object, the virtual model, and the positional relationship; identify a portion of the actual depth map that fails to match the expected depth map; and recognize a second object based on the identified portion.

In a second aspect, a robotic manipulator is utilized with the navigation system of the first aspect, wherein the robotic manipulator supports a surgical tool and comprises a plurality of links and a plurality of actuators configured to move the links to move the surgical tool, and wherein the robotic manipulator is controlled to avoid the second object.

In a third aspect, a method of operating a navigation system is provided, the navigation comprising a localizer configured to detect a position of a first object, a vision device configured to generate an actual depth map of surfaces near the first object, and a controller coupled to the localizer and the vision device, the method comprising: accessing a virtual model corresponding to the first object; identifying a positional relationship between the localizer and the vision device in a common coordinate system; generating an expected depth map of the vision device based on the detected position of the first object, the virtual model, and the positional relationship; identifying a portion of the actual depth map that fails to match the expected depth map; and recognize a second object based on the identified portion.

In a fourth aspect, a computer program product is provided comprising a non-transitory computer readable medium having instructions stored thereon, which when executed by one or more processors are configured to implement the method of the third aspect.

According to one implementation for any of the above aspects: the localizer is configured to be: an optical localizer configured to detect optical features associated with the first object; an electromagnetic localizer configured to detect electromagnetic features associated with the first object; an ultrasound localizer configured to detect the first object with or without any tracker; an inertial localizer configured to detect inertial features associated with the first object; or any combination of the aforementioned.

According to one implementation for any of the above aspects: the first object can be any of: an anatomy or bone of a patient; equipment in the operating room, such as, but not limited to: a robotic manipulator, a hand-held instrument, an end effector or tool attached to the robotic manipulator, a surgical table, a mobile cart, an operating table onto which the patient can be placed, an imaging system, a retractor, or any combination of the aforementioned.

According to one implementation for any of the above aspects: the vision device is coupled to any of: the localizer; a separate unit from the localizer; a camera unit of the navigation system; an adjustable arm; the robotic manipulator; an end effector; a hand-held tool; a surgical boom system, such as a ceiling mounted boom, a limb holding device, or any combination of the aforementioned.

According to one implementation for any of the above aspects, the surfaces near the first object can be surfaces: adjacent to the first object; spaced apart from the first object by a distance; touching the first object; directly on top of the first object; located in an environment near the first object; located in an environment behind or surrounding the first object; within a threshold distance of the first object; within a field of view of the localizer; or any combination of the aforementioned.

According to one implementation for any of the above aspects: the second object can be object that can form an obstacle, including any of: a second portion of the anatomy of the patient, such as surrounding soft tissue; equipment in the operating room, such as, but not limited to: a robotic manipulator, one or more arms of the robotic manipulator, a second robotic manipulator, a hand-held instrument, an end effector or tool attached to the robotic manipulator or hand-held instrument, a surgical table, a mobile cart, an operating table onto which the patient can be placed, an imaging system, a retractor, the body of a tracking device; a body part of a human being in the operating room, or any combination of the aforementioned.

According to one implementation for any of the above aspects: the controller can be one or more controllers or a control system. According to one implementation, the controller is configured to identify a position of the second object relative to the first object in the common coordinate system. According to one implementation, the controller identifies so based on the detected position of the first object, a location of the second object in the actual depth map, and the positional relationship.

According to one implementation, the first object defines a target volume of patient tissue to be treated according to a surgical plan. According to one implementation, the controller is configured to: determine whether the second object is an obstacle to treating the target volume according to the surgical plan based on the position of the second object relative to the target volume in the common coordinate system and the surgical plan. According to one implementation, responsive to determining that the second object is an obstacle to the surgical plan, the controller is configured to modify the surgical plan and/or trigger a notification and/or halt surgical navigation.

According to one implementation, a tracker is coupled to the first object. According to one implementation, the controller is configured to: detect, via the localizer, a position of the tracker in a first coordinate system specific to the localizer. According to one implementation, the controller can identify a position of the virtual model in the first coordinate system based on the detected position of the tracker in the first coordinate system and a positional relationship between the tracker and the first object in the first coordinate system. According to one implementation, the controller transforms the position of the virtual model in the first coordinate system to a position of the virtual model in a second coordinate system specific to the vision device based on the position of the virtual model in the first coordinate system and a positional relationship between the localizer and the vision device in the second coordinate system. According to one implementation, the controller can generate the expected depth map based on the position of the virtual model in the second coordinate system.

According to one implementation, the controller is configured to identify a portion of the actual depth map that fails to match the expected depth map by being configured to: compare the actual depth map and the expected depth map. In some implementations, the controller computes a difference between the actual depth map and the expected depth map. According to one implementation, the controller determines whether a first section of the difference indicates an absolute depth greater than a threshold depth. According to one implementation, the controller identifies as the portion a second section of the actual depth map that corresponds to the first section of the difference responsive to determining that the first section of the difference indicates an absolute depth greater than threshold depth. According to one implementation, the threshold depth is non-zero.

According to one implementation, the controller is configured to identify the portion of the actual depth map that fails to match the expected depth map. In some implementations, the controller does so by being configured to determine whether a size of the first section is greater than a minimum size threshold. In some implementations, the controller identifies as the portion the second section responsive to the determining that the size of the first section is greater than the minimum size threshold.

According to one implementation, the controller is configured to recognize a second object based on the identified portion by being configured to match the identified portion with a predetermined profile corresponding to the second object.

According to one implementation, the portion of the actual depth map comprises an arrangement of features corresponding to the second object and located in a first position of the actual depth map. According to one implementation, the controller is configured to track movement of the second object by monitoring whether the arrangement of features moves to a second position that differs from the first position. According to one implementation, the controller monitors such in an additional actual depth map subsequently generated by the vision device.

According to one implementation, the controller is configured to generate a virtual boundary corresponding to the second object in the common coordinate system. According to one implementation, the virtual boundary provides a constraint. In some examples, the constraint is on a motion of an object, such as a surgical tool, a robotic manipulator, a working end of a robotic hand-held surgical device, an imaging device, or any other moveable equipment in the operating room. In some examples, the constraint is a keep-out boundary or a keep-in boundary.

According to one implementation, the controller is configured to crop the actual depth map to a region of interest based on the virtual model, the detected position of the first object, and the positional relationship between the localizer and the vision device in a common coordinate system. In some implementations, the controller is configured to compare the actual depth map by being configured to compare the cropped actual depth map.

According to one implementation, the controller is configured to identify the positional relationship between the localizer and the vision device in the common coordinate system by being configured to project a pattern onto a surface in view of the vision device, and optionally also within view of the localizer. In some implementations, the controller generates localization data using the localizer indicating a position of the pattern in a first coordinate system specific to the localizer. In some implementations, the controller receives a calibration depth map illustrating the projected pattern generated by the vision device. In some implementations, the controller identifies a position of the projected pattern in a second coordinate system specific to the vision device based on the calibration depth map. In some implementations, the controller identifies the positional relationship between the localizer and the vision device in the common coordinate system based on the position of the pattern in the first coordinate system and the position of the pattern in the second coordinate system. In some implementations, the controller is configured to operate in a first spectral band to detect the position of the first object, the vision device is configured to operate in a second spectral band to generate the actual depth map of the surfaces near the first object, and the first spectral band differs from the second spectral band.

Any of the above aspects can be combined in full or in part. Any of the above aspects can be combined in full or in part.

The above summary may present a simplified overview of some aspects of the invention in order to provide a basic understanding of certain aspects the invention discussed herein. The summary is not intended to provide an extensive overview of the invention, nor is it intended to identify any key or critical elements or delineate the scope of the invention. The sole purpose of the summary is merely to present some concepts in a simplified form as an introduction to the detailed description presented below.

BRIEF DESCRIPTION OF THE DRAWINGS

FIG. 11 is an illustration of a virtual model corresponding to surgical retractors identified in the actual depth map of FIG. 9.

FIG. 12 is an illustration of a virtual model corresponding to a ligament identified in the actual depth map of FIG. 9.

DETAILED DESCRIPTION

Figure 1:
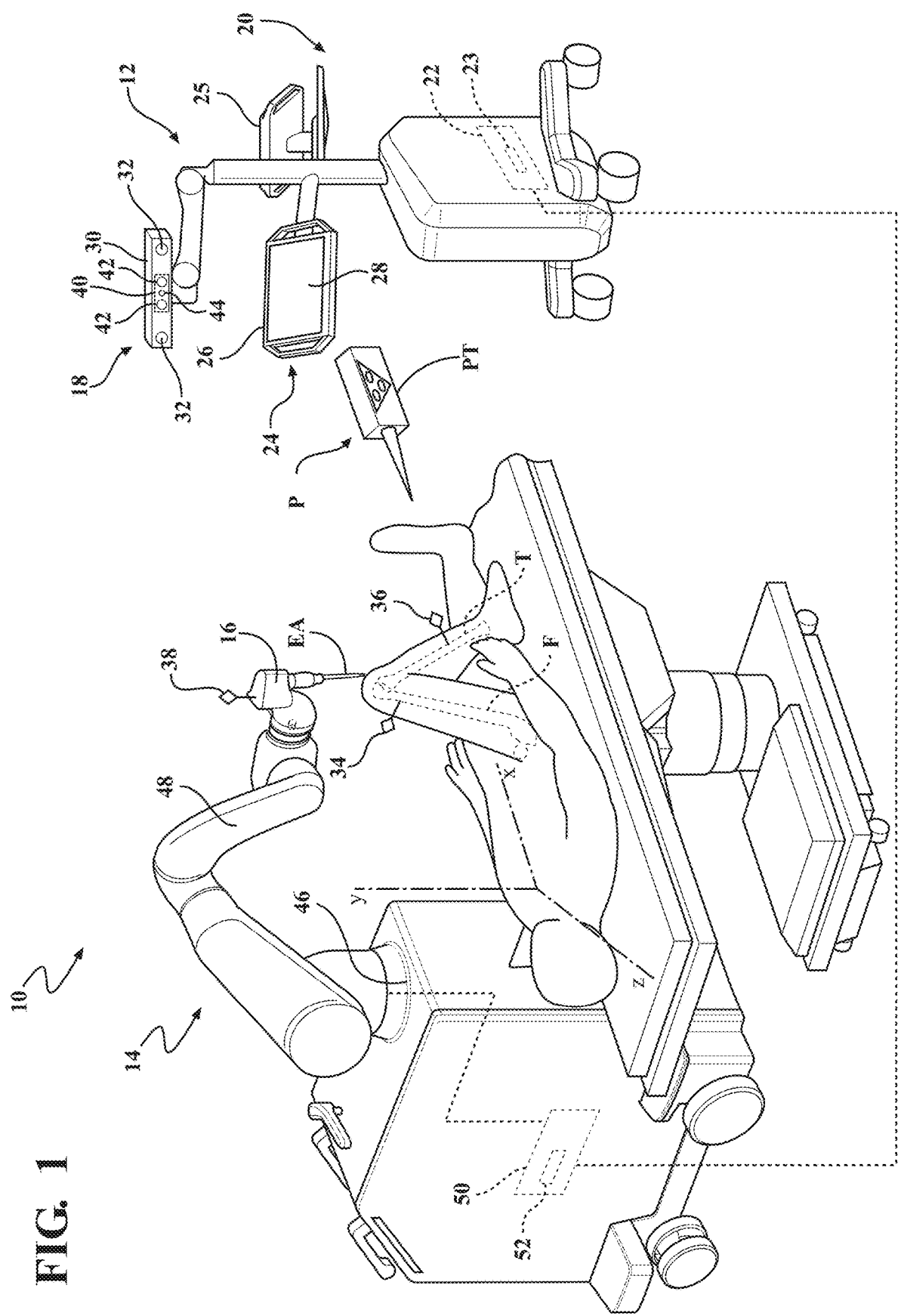
FIG. 1 is a perspective view of a surgical navigation system including a localizer and a vision device.

FIG. 1 illustrates a surgical system 10 for treating a patient. The surgical system 10 may be located in a surgical setting such as an operating room of a medical facility. The surgical system 10 may include a surgical navigation system 12 and a robotic manipulator 14. The robotic manipulator 14 may be coupled to a surgical instrument 16, and may be configured to maneuver the surgical instrument 16 to treat a target volume of patient tissue, such as at the direction of a surgeon and/or the surgical navigation system 12. For example, the surgical navigation system 12 may cause the robotic manipulator 14 to maneuver the surgical instrument 16 to remove the target volume of patient tissue while avoiding other objects adjacent the target volume, such as other medical tools and adjacent anatomical structures. Alternatively, the surgeon may manually hold and maneuver the surgical instrument 16 while receiving guidance from the surgical navigation system 12. As some non-limiting examples, the surgical instrument 16 may be a burring instrument, an electrosurgical instrument, an ultrasonic instrument, a reamer, an impactor, or a sagittal saw.

During a surgical procedure, the surgical navigation system 12 may track the position (location and orientation) of objects of interest within a surgical workspace using a combination of tracker-based localization and machine vision. The surgical workspace for a surgical procedure may be considered to include the target volume of patient tissue being treated and the area immediately surrounding the target volume being treated in which an obstacle to treatment may be present. The tracked objects may include, but are not limited to, anatomical structures of the patient, target volumes of anatomical structures to be treated, surgical instruments such as the surgical instrument 16, and anatomical structures of surgical personal such as a surgeon's hand or fingers. The tracked anatomical structures of the patient and target volumes may include soft tissue such as ligaments, muscle, and skin, may include hard tissue such bone. The tracked surgical instruments may include retractors, cutting tools, and waste management devices used during a surgical procedure.

Fixing trackers to objects of interest in a surgical workspace may provide an accurate and efficient mechanism for the surgical navigation system 12 to determine the position of such objects in the surgical workspace. During the procedure, the trackers may generate known signal patterns, such as in a particular non-visible light band (e.g., infrared, ultraviolet). The surgical navigation system 12 may include a localizer that is specific to detecting signals in the particular non-visible light band and ignores light signals outside of this band. Responsive to the localizer detecting the signal pattern associated with a given tracker, the surgical navigation system 12 may determine a position of the tracker relative to the localizer based on the angle at which the pattern is detected. The surgical navigation system 12 may then infer the position of an object to which the tracker is affixed based on the determined position of the tracker and a fixed positional relationship between the object and the tracker.

While the above trackers may enable the surgical navigation system 12 to accurately and efficiently track hard tissue objects such as bone and surgical instruments in the surgical workspace, these trackers are generally not adequate for tracking soft tissue objects such as skin and ligaments. Specifically, due to the flexible nature of soft tissue objects, maintaining a fixed positional relationship between an entire soft tissue object and a tracker during the course of a surgical procedure is difficult. Moreover, attaching a tracker to each of the several patient tissues and instruments involved in a surgical procedure congests the surgical workspace making it difficult to navigate, and increases the cost and complexity of the surgical navigation system 12. Accordingly, in addition to tracker-based localization, the surgical navigation system 12 may also implement machine vision to track objects in a surgical workspace during a surgical procedure.

Specifically, in addition to detecting the position of objects in a surgical workspace using a localizer and affixed trackers, the surgical navigation system 12 may include a vision device configured to generate a depth map of surfaces in a workspace (also referred to herein as a target site). The target site can be various different objects or sites. In one example, the target site is a surgical site, such as a portion of anatomy (e.g., bone) requiring treatment or tissue removal. In other examples, the target site can be an equipment in the operating room, such as the robotic manipulator, the end effector or tool attached to the robotic manipulator, a surgical table, a mobile cart, an operating table onto which the patient can be placed, an imaging system, or the like.

The surgical navigation system 12 may also be configured to identify a positional relationship between the localizer and the vision device in a common coordinate system, and may be configured to generate an expected depth map of the vision device based on a detected position of an object in the target site using the localizer, a virtual model corresponding to the object, and the positional relationship. Thereafter, the surgical navigation system 12 may be configured to compare the expected depth map to an actual depth map generated by the vision device, and to identify a portion of an actual depth map that fails to match the estimated depth map based on the comparison. The surgical navigation system 12 may be configured to then identify an object in the target site based on the identified portion, and to determine whether the object is an obstacle to a current surgical plan.

The surgical navigation system 12 may display the relative positions of objects tracked during a surgical procedure to aid the surgeon. The surgical navigation system 12 may also control and/or constrain movement of the robotic manipulator 14 and/or surgical instrument 16 to virtual boundaries associated with the tracked objects. For example, the surgical navigation system 12 may identify a target volume of patient tissue to be treated and potential obstacles in the surgical workspace based on the tracked objects. The surgical navigation system 12 may then restrict a surgical tool (e.g., an end effector EA of the surgical instrument 16) from contacting anything beyond the target volume of patient tissue to be treated, improving patient safety and surgical accuracy. The surgical navigation system 12 may also eliminate damage to surgical instruments caused by unintended contact with other objects, which may also result in undesired debris at the target site.

As illustrated in FIG. 1, the surgical navigation system 12 may include a localizer 18 and a navigation cart assembly 20. The navigation cart assembly 20 may house a navigation controller 22 configured to implement the functions, features, and processes of the surgical navigation system 12 described herein. In particular, the navigation controller 22 may include a processor 23 programmed to implement the functions, features, and processes of the navigation controller 22 and surgical navigation system 12 described herein. For example, the processor 23 may be programmed to convert optical-based signals received from the localizer 18 into localizer data representative of the position of objects affixed to trackers in the surgical workspace.

The navigation controller 22 may be in operative communication with a user interface 24 of the surgical navigation system 12. The user interface 24 may facilitate user interaction with the surgical navigation system 12 and navigation controller 22. For example, the user interface 24 may include one or more output devices that provide information to a user, such as from the navigation controller 22. The output devices may include a display 25 adapted to be situated outside of a sterile field including the surgical workspace and may include a display 26 adapted to be situated inside the sterile field. The displays 25, 26 may be adjustably mounted to the navigation cart assembly 20. The user interface 24 may also include one or more input devices that enable user-input to the surgical navigation system 12. The input devices may include a keyboard, mouse, and/or touch screen 28 that can be interacted with by a user to input surgical parameters and control aspects of the navigation controller 22. The input devices may also include a microphone that enables user-input through voice-recognition technology.

The localizer 18 may be configured to detect the position of one or more objects affixed to trackers in the surgical workspace, such as by detecting the position of the trackers affixed to the objects. Specifically, the localizer 18 may be coupled to the navigation controller 22 of the surgical navigation system 12, and may generate and communicate optical-based signals to the navigation controller 22 that indicate the position of the one or more trackers in the surgical workspace. The navigation controller 22 may then be configured to generate localizer data indicative of the position of the objects affixed to the trackers in the surgical workspace based on the optical-based signals and fixed positional relationships between the objects and trackers. Objects in the target site tracked with the localizer 18 may be referred to herein as "localized objects."

The localizer 18 may have an outer casing 30 that houses at least two optical sensors 32. Each of the optical sensors 32 may be adapted to detect signals in a particular non-visible light band specific to the trackers, such as infrared or ultraviolet. While FIG. 1 illustrates the localizer 18 as a single unit with multiple optical sensors 32, in an alternative example, the localizer 18 may include separate units arranged around the surgical workspace, each with a separate outer casing and one or more optical sensors 32.

The optical sensors 32 may be one-dimensional or two-dimensional charge-coupled devices (CCDs). For example, the outer casing 30 may house two two-dimensional CCDs for triangulating the position of trackers in the surgical workplace, or may house three one-dimensional CCDs for triangulating the position of trackers in the surgical workplace. Additionally, or alternatively, the localizer 18 may employ other optical sensing technologies, such as complementary metal-oxide semiconductor (CMOS) active pixels.

In some implementations, the navigation system and/or localizer 18 are electromagnetically (EM) based. For example, the navigation system may comprise an EM transceiver coupled to the navigation controller 22 and/or to another computing device, controller, and the like. Here, the trackers may comprise EM components attached thereto (e.g., various types of magnetic trackers, electromagnetic trackers, inductive trackers, and the like), which may be passive or may be actively energized. The EM transceiver generates an EM field, and the EM components respond with EM signals such that tracked states are communicated to (or interpreted by) the navigation controller 22. The navigation controller 22 may analyze the received EM signals to associate relative states thereto. Here too, it will be appreciated that embodiments of EM-based navigation systems may have structural configurations that are different than the active marker-based navigation system illustrated herein.

In other implementations, the navigation system and/or the localizer 18 could be based on one or more types of imaging systems that do not necessarily require trackers to be fixed to objects in order to determine location data associated therewith. For example, an ultrasound-based imaging system could be provided to facilitate acquiring ultrasound images (e.g., of specific known structural features of tracked objects, of markers or stickers secured to tracked objects, and the like) such that tracked states (e.g., position, orientation, and the like) are communicated to (or interpreted by) the navigation controller 22 based on the ultrasound images. The ultrasound images may be 2D, 3D, or a combination thereof. The navigation controller 22 may process ultrasound images in near real-time to determine the tracked states. The ultrasound imaging device may have any suitable configuration and may be different than the camera unit as shown in FIG. 1. By way of further example, a fluoroscopy-based imaging system could be provided to facilitate acquiring X-ray images of radio-opaque markers (e.g., stickers, tags, and the like with known structural features that are attached to tracked objects) such that tracked states are communicated to (or interpreted by) the navigation controller 22 based on the X-ray images. The navigation controller 22 may process X-ray images in near real-time to determine the tracked states. Similarly, other types of optical-based imaging systems could be provided to facilitate acquiring digital images, video, and the like of specific known objects (e.g., based on a comparison to a virtual representation of the tracked object or a structural component or feature thereof) and/or markers (e.g., stickers, tags, and the like that are attached to tracked objects) such that tracked states are communicated to (or interpreted by) the navigation controller 22 based on the digital images. The navigation controller 22 may process digital images in near real-time to determine the tracked states.

Accordingly, it will be appreciated that various types of imaging systems, including multiple imaging systems of the same or different type, may form a part of the navigation system without departing from the scope of the present disclosure. Those having ordinary skill in the art will appreciate that the navigation system and/or localizer 18 may have any other suitable components or structure not specifically recited herein. For example, the navigation system may utilize solely inertial tracking or any combination of tracking techniques. Furthermore, any of the techniques, methods, and/or components associated with the navigation system illustrated in FIG. 1 may be implemented in a number of different ways, and other configurations are contemplated by the present disclosure.

The localizer 18 may be mounted to an adjustable arm to selectively position the optical sensors 32 with a field of view of the surgical workspace and target volume that, ideally, is free from obstacles. The localizer 18 may be adjustable in at least one degree of freedom by rotating about a rotational joint and may be adjustable about two or more degrees of freedom.

As previously described, the localizer 18 may cooperate with a plurality of tracking devices, also referred to herein as trackers, to determine the position of objects within the surgical workspace to which the trackers are affixed. In general, the object to which each tracker is affixed may be rigid and inflexible so that movement of the object cannot or is unlikely to alter the positional relationship between the object and the tracker. In other words, the relationship between a tracker in the surgical workspace and an object to which the tracker is attached may remain fixed, notwithstanding changes in the position of the object within the surgical workspace. For instance, the trackers may be firmly affixed to patient bones and surgical instruments, such as retractors and the surgical instrument 16. In this way, responsive to determining a position of a tracker in the surgical workspace using the localizer 18, the navigation controller 22 may infer the position of the object to which the tracker is affixed based on the determined position of the tracker.

For example, when the target volume to be treated is located at a patient's knee area, a tracker 34 may be firmly affixed to the femur F of the patient, a tracker 36 may be firmly affixed to the to the tibia T of the patient, and a tracker 38 may be firmly affixed to the surgical instrument 16. Trackers 34, 36 may be attached to the femur F and tibia T in the manner shown in U.S. Pat. No. 7,725,162, hereby incorporated by reference. Trackers 34, 36 may also be mounted like those shown in U.S. Patent Application Publication No. 2014/0200621, filed on Jan. 16, 2014, entitled, "Navigation Systems and Methods for Indicating and Reducing Line-of-Sight Errors," hereby incorporated by reference. A tracker 38 may be integrated into the surgical instrument 16 during manufacture or may be separately mounted to the surgical instrument 16 in preparation for a surgical procedure.

Prior to the start of a surgical procedure using the surgical system 10, pre-operative images may be generated for anatomy of interest, such as anatomical structures defining and/or adjacent a target volume of patient tissue to be treated by the surgical instrument 16. For example, when the target volume of patient tissue to be treated is in a patient's knee area, pre-operative images of the patient's femur F and tibia T may be taken. These images may be based on MRI scans, radiological scans, or computed tomography (CT) scans of the patient's anatomy, and may be used to develop virtual models of the anatomical structures. Each virtual model for an anatomical structure may include a three-dimensional model (e.g., point cloud, mesh, CAD) that includes data representing the entire or at least a portion of the anatomical structure, and/or data representing a target volume of the anatomical structure to be treated. These virtual models may be provided to and stored in the navigation controller 22 in advance of a surgical procedure.

In addition or alternatively to taking pre-operative images, plans for treatment can be developed in the operating room from kinematic studies, bone tracing, and other methods. These same methods could also be used to generate the virtual models described above.

In addition to virtual models corresponding to the patient's anatomical structures of interest, prior to the surgical procedure, the navigation controller 22 may receive and store virtual models for other tracked objects of interest to the surgical procedure, such as surgical instruments and other objects potentially present in the surgical workspace (e.g., the surgeon's hand and/or fingers). The navigation controller 22 may also receive and store surgical data particular to the surgical procedure, such as positional relationships between trackers and the objects fixed to the trackers, a positional relationship between the localizer 18 and the vision device, and a surgical plan. The surgical plan may identify the patient anatomical structures involved in the surgical procedure, may identify the instruments being used in the surgical procedure, and may define the planned trajectories of instruments and the planned movements of patient tissue during the surgical procedure.

During the surgical procedure, the optical sensors 32 of the localizer 18 may detect light signals, such as in a non-visible light band (e.g., infrared or ultraviolet), from the trackers 34, 36, 38, and may output optical-based signals to the navigation controller 22 indicating the position of the trackers 34, 36, 38 relative to the localizer 18 based on the detected light signals. The navigation controller 22 may then generate localizer data indicating the positions of the objects fixed to the trackers 34, 36, 38 relative to the localizer 18 based on the determined positions of the trackers 34, 36, 38 and the known positional relationships between the trackers 34, 36, 38 and the objects.

To supplement the tracker-based object tracking provided by the localizer 18, the surgical navigation system 12 may also include the vision device 40. The vision device 40 may be capable of generating three-dimensional images of the surgical workspace site in real time. Unlike the localizer 18, which may be limited to detecting and pinpointing the position of non-visible light signals transmitted from the trackers 34, 36, 38, the vision device 40 may be configured to generate a three-dimensional image of the surfaces in and surrounding the target volume that are in the field of view of the vision device 40, such as in the form of a depth map. The vision device 40 may include one or more image sensors 42 and a light source 44. Each of the image sensors 42 may be a CMOS sensor.

For example, the vision device 40 may generate a depth map of the surgical workspace by illuminating exposed surfaces in the surgical workspace with non-visible light, such as infrared or ultraviolet light. The surfaces may then reflect back the non-visible light, which may be detected by the one or more image sensors 42 of the vision device 40. Based on a time of flight of the non-visible light from transmission to detection by the vision device 40, the vision device 40 may determine a distance between the vision device 40 and several points on the exposed surfaces of the surgical workspace. The vision device 40 may then generate a depth map indicating the distance and angle between the vision device 40 and each surface point. Alternatively, the vision device 40 may utilize other modalities to generate a depth map, such as and without limitation, structured light projections, laser range finding, or stereoscopy.

Similar to the localizer 18, prior to a surgical procedure, the vision device 40 may be positioned with a field of view of the surgical workspace preferable without obstacles. The vision device 40 may be integrated with the localizer 18, as illustrated in FIG. 1. Alternatively, the vision device 40 may be mounted to a separate adjustable arm to position the vision device 40 separately from the localizer 18. The vision device 40 can also be directly attached to the robotic manipulator 14, such as, for example, as described in U.S. Pat. No. 10,531,926, entitled "Systems and Methods for Identifying and Tracking Physical Objects During a Robotic Surgical Procedure", the contents of which are hereby incorporated by reference in its entirety. The vision device 40 may also be in operative communication with the navigation controller 22.

As described above, the navigation controller 22 may be configured to track objects and identify obstacles in the surgical workspace based on the tracker-based localization data generated using the localizer 18 and depth maps generated by the vision device 40. In particular, at the same time vision time the vision device 40 generates a depth map of the surgical workspace, the localizer 18 may generate optical-based data used to generate the localizer data indicating the position of objects fixed to trackers in the surgical workspace relative to the localizer 18. The depth maps generated by the vision device 40 and the localizer data generated with the localizer 18 may thus be temporally interleaved. In other words, each instance of localizer data generated with the localizer 18 may be temporally associated with a different depth map generated by the vision device 40, such that the positions of objects indicated in the localizer data and the positions of those objects in the associated depth map correspond to a same moment in time during the surgical procedure.

Responsive to determining the localizer data, the navigation controller 22 may be configured to generate an expected depth map to be captured by the vision device 40 and associated with the localization data. The expected depth map may be the depth map expected to be generated by the vision device 40 that is temporally associated with the localizer data, assuming only the objects fixed to the trackers are present in the surgical workspace. The navigation controller 22 may be configured to determine the expected depth map based on the detected positions of objects fixed to trackers in the surgical workspace as indicated in the localizer data, virtual models corresponding to the objects, and a positional relationship between the localizer 18 and the vision device 40.

Thereafter, the navigation controller 22 may retrieve the actual depth map generated by the vision device 40 that is temporally associated with the localizer data, and may identify a portion of the actual depth map that fails to match the expected depth map. The navigation controller 22 may then identify objects in the surgical workspace, such as objects other than the objects fixed to trackers that are adjacent to a target volume of patient tissue to be treated, based on the identified portion, and may determine whether any such objects poses an obstacle to a current surgical trajectory.

The surgical instrument 16 may form part of an end effector of the robotic manipulator 14. The robotic manipulator 14 may include a base 46, several links 48 extending from the base 46, and several active joints for moving the surgical instrument 16 with respect to the base 46. The links 48 may form a serial arm structure as shown in FIG. 1, a parallel arm structure (shown for example in FIG. 3), or other suitable structure. The robotic manipulator 14 may include an ability to operate in a manual mode in which a user grasps the end effector of the robotic manipulator 14 to cause movement of the surgical instrument 16 (e.g., directly, or through force/torque sensor measurements that cause active driving of the robotic manipulator 14). The robotic manipulator 14 may also include a semi-autonomous mode in which the surgical instrument 16 is moved by the robotic manipulator 14 along a predefined tool path (e.g., the active joints of the robotic manipulator 14 are operated to move the surgical instrument 16 without requiring force/torque on the end effector from the user). An example of operation in a semi-autonomous mode is described in U.S. Pat. No. 9,119,655 to Bowling, et al., hereby incorporated by reference. A separate tracker may be attached to the base 46 of the robotic manipulator 14 to track movement of the base 46 by the localizer 18.

Similar to the surgical navigation system 12, the robotic manipulator 14 may house a manipulator controller 50 including a processor 52 programmed to implement the processes of the robotic manipulator 14, or more particularly the manipulator controller 50, described herein. For example, the processor 52 may be programmed to control operation and movement of the surgical instrument 16 through movement of the links 48, such as at the direction of the surgical navigation system 12.

During a surgical procedure, the manipulator controller 50 may be configured to determine a desired location to which the surgical instrument 16 should be moved, such as based on navigation data received from the navigation controller 22. Based on this determination, and information relating to the current position of the surgical instrument 16, the manipulator controller 50 may be configured to determine an extent to which each of links 48 needs to be moved to reposition the surgical instrument 16 from the current position to the desired position. Data indicating where the links 48 are to be repositioned may be forwarded to joint motor controllers (e.g., one for controlling each motor) that control the active joints of the robotic manipulator 14. Responsive to receiving such data, the joint motor controllers may be configured to move the links 48 in accordance with the data, and consequently move the surgical instrument 16 to the desired position.

Figure 2:
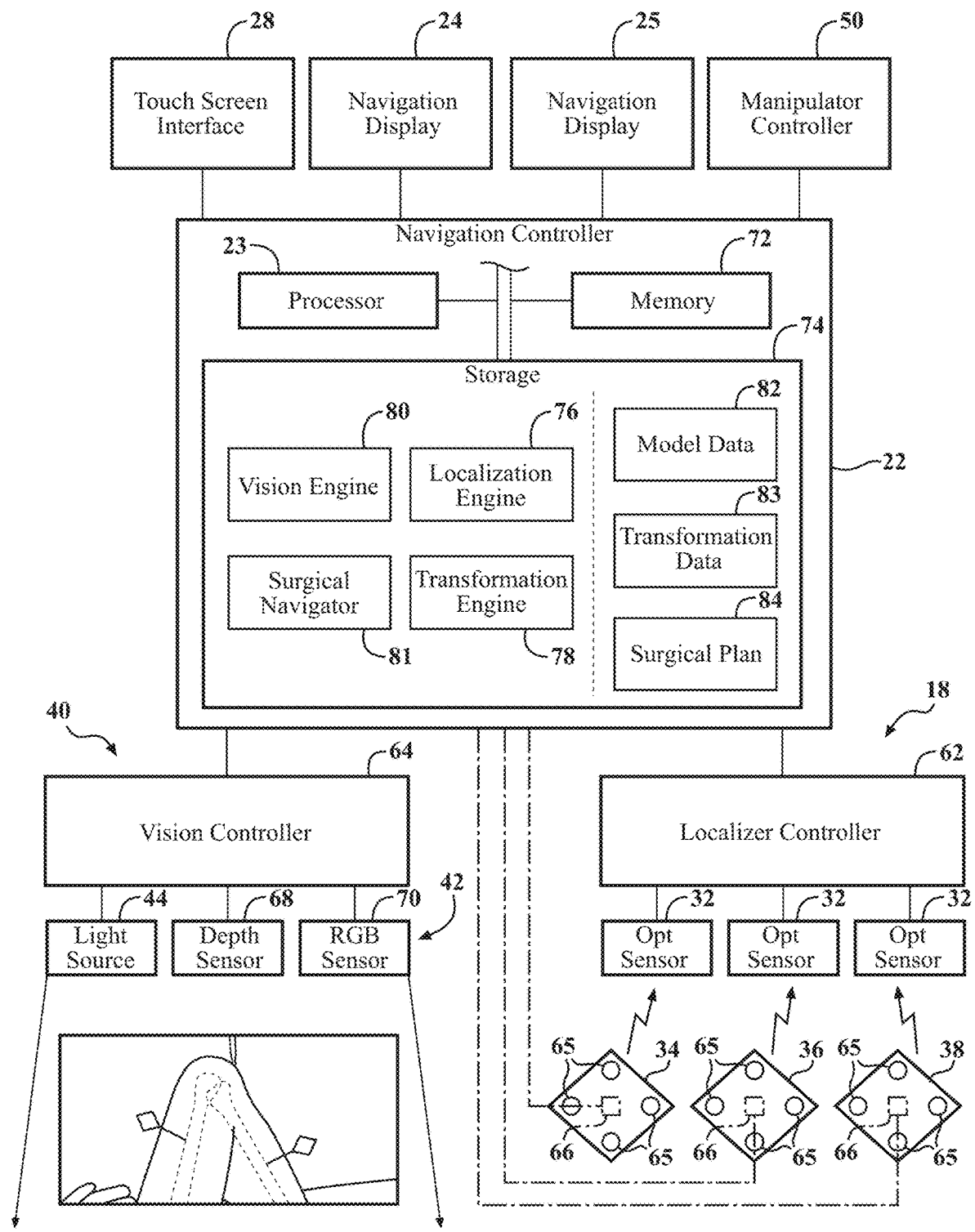
FIG. 2 is a schematic view of a control system for controlling the surgical navigation system of FIG. 1.

Referring now to FIG. 2, the localizer 18 and vision device 40 may include a localizer controller 62 and vision controller 64 respectively. The localizer controller 62 may be communicatively coupled to the optical sensors 32 of the localizer 18 and to the navigation controller 22. During a surgical procedure, the localizer controller 62 may be configured to operate the optical sensors 32 to cause them to generate optical-based data indicative of light signals received from the trackers 34, 36, 38.

The trackers 34, 36, 38 may be active trackers each having at least three active markers for transmitting light signals to the optical sensors 32. The trackers 34, 36, 38 may be powered by an internal battery, or may have leads to receive power through the navigation controller 22. The active markers of each tracker 34, 36, 38 may be light emitting diodes (LEDs) 65 that transmit light, such as infrared or ultraviolet light. Each of the trackers 34, 36, 38 may also include a tracker controller 66 connected to the LEDs 65 of the tracker 34, 36, 38 and to the navigation controller 22.

The tracker controller 66 may be configured to control the rate and order in which LEDs 65 of the trackers 34, 36, 38 fire, such as at the direction of the navigation controller 22. For example, the tracker controllers 66 of the trackers 34, 36, 38 may cause the LEDs 65 of each tracker 34, 36, 38 to fire at different rates and/or times to facilitate differentiation of the trackers 34, 36, 38 by the navigation controller 22.

The sampling rate of the optical sensors 32 is the rate at which the optical sensors 32 receive light signals from sequentially fired LEDs 65. The optical sensors 32 may have sampling rates of 100 Hz or more, or more preferably 300 Hz or more, or most preferably 500 Hz or more. For example, the optical sensors 32 may have sampling rates of 8000 Hz.

Rather than being active trackers, the trackers 34, 36, 38 may be passive trackers including passive markers (not shown), such as reflectors that reflect light emitted from the localizer 18 (e.g., light emitted from the light source 44 (FIG. 1)). The reflected light may then be received by the optical sensors 32.

Responsive to the optical sensors 32 receiving light signals from the trackers 34, 36, 38, the optical sensors 32 may output optical-based data to the localizer controller 62 indicating the position of trackers 34, 36, 38 relative to the localizer 18, and correspondingly, indicating the position of the objects firmly affixed to the trackers 34, 36, 38 relative to the localizer 18. In particular, each optical sensor 32 may include a one- or two-dimensional sensor area that detects light signals from the trackers 34, 36, 38, and responsively indicates a position within the sensor area that each light signal is detected. The detection position of each light signal within a given sensor area may be based on the angle at which the light signal is received by the optical sensor 32 including the sensor area, and similarly may correspond to the position of the source of the light signal in the surgical workspace.

Thus, responsive to receiving light signals from the trackers 34, 36, 38, each optical sensor 32 may generate optical-based data indicating positions within the sensor area of the optical sensor 32 that the light signals were detected. The optical sensors 32 may communicate such optical-based data to the localizer controller 62, which may then communicate the optical-based data to the navigation controller 22. The navigation controller 22 may then generate tracker position data indicating the positions of the trackers 34, 36, 38 relative to the localizer 18 based on the optical-based data. For example, the navigation controller 22 may triangulate the positions of the LEDs 65 relative to the localizer 18 based on the optical-based data, and may apply stored positional relationships between the trackers 34, 36, 38 and the markers to the determined positions of the LEDs 65 relative to the localizer 18 to determine positions of the trackers 34, 36, 38 relative to the localizer 18.

Thereafter, the navigation controller 22 may generate the localizer data indicating the positions of the objects firmly affixed to the trackers 34, 36, 38 relative to the localizer 18 based on the tracker position data. Specifically, the navigation controller 22 may retrieve stored positional relationships between the trackers 34, 36, 38 and the objects to which the trackers 34, 36, 38 are affixed, and may apply these positional relationships to the tracker position data to determine the position of the objects fixed to the trackers 34, 36, 38 relative to the localizer 18. Alternatively, the localizer controller 62 may be configured determine the tracker position data and/or localizer data based on the received optical-based data, and may transmit the tracker position data and/or localizer data to the navigation controller 22 for further processing.

The vision controller 64 may be communicatively coupled to the light source 44 and the one or more image sensors 42 of the vision device 40, and to the navigation controller 22. Contemporaneously with the localizer controller 62 causing the localizer 18 to generate optical-based data indicating the position of the trackers 34, 36, 38 in the surgical workspace, the vision controller 64 may cause the vision device 40 to generate a depth map of the exposed surfaces of the surgical workspace. Specifically, the vision controller 64 may cause the image sensors 42 to generate image data that forms the basis of the depth map, and may generate the depth map based on the image data. The vision controller 64 may then forward the depth map to the navigation controller 22 for further processing. Alternatively, the vision controller 64 may communicate the image data to the navigation controller 22, which may then generate the depth map based on the received image data.

In general, a depth map generated by the vision device 40 may indicate the distance between the vision device 40 and surfaces in the field of view of the vision device 40. In other words, the depth map may illustrate a topography of the surfaces in the surgical workspace form the viewpoint of the vision device 40. Each depth map generated by the vision device 40 may include a plurality of image components forming an image frame of the vision device 40. Each of the image components may be akin to a pixel of the depth map, and may define a vector from a center of the vision device 40 to a point on a surface in the field of view of vision device. For instance, the location of the image component in the image frame of the vision device 40 may correspond to the horizontal and vertical components of the vector defined by the image component, and a color of the image component may correspond to the depth component of the vector defined by the image component. As an example, image components representing surface points in the surgical workspace closer to the vision device 40 may have a brighter color than those image components representing surface points farther from the vision device 40.

The vision device 40 may be a depth camera including one or more depth sensors 68. The depth sensors 68 may be adapted to detect light, such as non-visible light, reflected off surfaces within the field of view of the depth sensors 68. During a surgical procedure, the vision controller 64 may cause the light source 44 to illuminate the target site with non-visible light, such as infrared or ultraviolet light. The depth sensors 68 may then detect reflections of the non-visible light off the surfaces the target site, which may enable the vision controller 64 to generate the depth map.

For example, the vision controller 64 may generate a depth map based on a time for the light transmitted from the light source 44 to reflect off points on exposed surfaces in the target site (i.e., time of flight methodology), which may correspond to distances between the vision device 40 and the various points. The vision controller 64 may then utilize these determined distances to generate the depth map. As an alternative example, the light source 44 may project a known structured non-visible light pattern onto exposed surfaces in the surgical site. The depth sensors 68 may then detect a reflection of the known pattern, which may be distorted based on the topography of the surfaces in the target site. The vision controller 64 may thus be configured to generate the depth map of the target site based on a comparison between the known pattern and the distorted version of the pattern detected by the depth sensors 68.

Alternatively, the vision device 40 may be an RGB camera including one or more RGB sensors 70. The RGB sensors 70 may be configured to generate color images of the exposed surfaces in the target site, and the vision controller 64 may be configured to generate the depth made based on the color images.

For instance, similar to the structured light methodology described above, the vision controller 64 may be configured to cause the light source 44 to project a known structured light pattern onto the target site, such as in a color that deviates from colors in the target site. The RGB sensors 70 may then generate an RGB image of the target site, which may depict a distorted version of the known structured light pattern based on the surface topography of the of the target site. The vision controller 64 may extract the distorted version of the known structured light pattern from the RGB image, such as using pattern recognition, edge detection, and color recognition, and may determine the depth map based on a comparison between the known structured light pattern and the extracted distorted version.

As a further alternative, the vision device 40 may be configured to generate a depth map of the target site using principles in stereoscopy. More particularly, multiple image sensors 42, such as multiple depth sensors 68 or RGB sensors 70, may be positioned to have fields of view of the target site from different angles. The vision controller 64 may be configured to cause each image sensor 42 to simultaneously generate an image of the target site from the different angle. For instance, when the image sensors 42 are depth sensors 68, the vision controller 64 may be configured to cause the light source 44 to illuminate the exposed surfaces of the target site with a pattern of non-visible light, and each of the depth sensors 68 may image the pattern of non-visible light reflected off the exposed surfaces from a different angle. The vision controller 64 may then determine a three-dimensional position of points on the surfaces in the target site relative to the vision device 40 based on the position of the surface points in each image and a known positional relationship between image sensors 42. The vision controller 64 may thereafter generate the depth map based on the determined three-dimensional positions.

To reduce inference between the localizer 18 and vision device 40 during the surgical procedure, the localizer 18 and vision device 40 may be configured to operate in different spectral bands to detect the positions of objects in the target site. Additionally, or alternatively, when vision device 40 uses a light source 44 to illuminate the exposed surfaces in the target site, such as when the vision device 40 operates in a non-visible light band, the localizer 18 may be configured to operate with a temporal exposure rate sufficiently short so that the light source 44 of the vision device 40 is not visible of the localizer 18.

As previously described, the navigation controller 22 may include a processor 23 programmed to perform the functions, features, and processes of the navigation controller 22 described herein, such as calculating an expected depth map based on localizer data generated using the localizer 18, and determining objects adjacent to a target volume of patient tissue to be treated in a surgical site by comparing the expected depth map to an actual depth map generated by the vision device 40. In addition to the processor 23, the navigation controller 22 may include memory 72 and non-volatile storage 74 each operatively coupled to the processor 23.

The processor 23 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions stored in the memory 72. The memory 72 may include a single memory device or a plurality of memory devices including, but not limited to, read-only memory (ROM), random access memory (RAM), volatile memory, non-volatile memory, static random-access memory (SRAM), dynamic random-access memory (DRAM), flash memory, cache memory, or any other device capable of storing information. The non-volatile storage 74 may include one or more persistent data storage devices such as a hard drive, optical drive, tape drive, non-volatile solid-state device, or any other device capable of persistently storing information.

The non-volatile storage 74 may store software, such as a localization engine 76, a transformation engine 78, a vision engine 80, and a surgical navigator 81. The software may be embodied by computer-executable instructions compiled or interpreted from a variety of programming languages and/or technologies, including, without limitation, and either alone or in combination, Java, C, C++, C#, Objective C, Fortran, Pascal, Java Script, Python, Perl, and PL/SQL.

The processor 23 may operate under control of the software stored in the non-volatile storage 74. In particular, the processor 23 may be configured to execute the software as active running processes by reading into the memory 72 and executing the computer-executable instructions of the software. Upon execution by the processor 23, the computer-executable instructions may be configured to cause the processor 23 to implement the configured functions, features, and processes of the navigation controller 22 described herein. The software may thus be configured to cause the navigation controller 22 to implement the functions, features, and processes of the navigation controller 22 described herein by virtue of the computer-executable instructions of the software being configured, upon execution of the processor 23, to cause the processor 23 of the navigation controller 22 to implement the processes of the navigation controller 22 described herein.

The non-volatile storage 74 of the navigation controller 22 may also store data that facilitates operation of the navigation controller 22. Specifically, the software of the navigation controller 22 may be configured to access the data stored in the non-volatile storage 74, and to implement the functions, features, and processes of the navigation controller 22 described herein based on the data.

For example and without limitation, the data stored in the non-volatile storage 74 may include model data 82, transformation data 83, and surgical plan 84. The model data 82 may include the virtual models of anatomical structures of interest to the surgical procedure, including the virtual models for potential obstacles such as a surgeon's hand or fingers, and virtual models for the surgical instruments being used in a surgical procedure, as described above. The transformation data 83 may include the positional relationships herein, which may enable transforming a position of an object in the surgical workspace relative to one device, such as a tracker 34, 36, 38 or the localizer 18 or the vision device 40, to a position of the object relative to another device. For example, the transformation data 83 may set forth the fixed positional relationships between the trackers 34, 36, 38 and the objects firmly affixed to the trackers 34, 36, 38, and a positional relationship between localizer 18 and the vision device 40. The surgical plan 84 may identify patient anatomical structures target volumes involved in the surgical procedure, may identify the instruments being used in the surgical procedure, and may define the planned trajectories of instruments and the planned movements of patient tissue during the surgical procedure.

Referring again to the software running on the navigation controller 22, the localization engine 76 may be configured to generate the localization data indicative of the position of the objects firmly affixed to the trackers 34, 36, 38 relative to the localizer 18, such as based on optical-based data generated by the optical sensors 32 of the localizer 18. The transformation engine 78 may be configured to transform the position of an object relative to one device of the surgical system 10 to a position of the object relative to another device of the surgical system 10, such as based on the positional relationships represented by the transformation data 83. The vision engine 80 may be configured to generate an expected depth map based on localization data generated by the localization engine 76 and the transformation data 83, and to compare the expected depth map with an actual depth map generated by the vision device 40 to identify and track objects in the surgical workspace. The surgical navigator 81 may be configured to provide surgical guidance based on the identification and tracking determined by the vision engine 80. Further details of the functionality of these software components are discussed in more detail below.

Although not shown, each of the manipulator controller 50, the localizer controller 62, and the vision controller 64 may also include a processor, memory, and non-volatile storage including data and software configured, upon execution of its computer-executable instructions, to implement the functions, features, and processes of the controller described herein.

While an example surgical system 10 is shown in FIG. 1 and further detailed in FIG. 2, this example is not intended to be limiting. Indeed, the surgical system 10 may have more or fewer components, and alternative components and/or implementations may be used. For instance, all or a portion of the of the localizer engine 76 may be implemented by the localizer controller 62. As an example, the localizer controller 62 may be configured to generate the localizer data indicating the positions of objects firmly affixed to the trackers 34, 36, 38 based on the model data 82.

Figure 3:
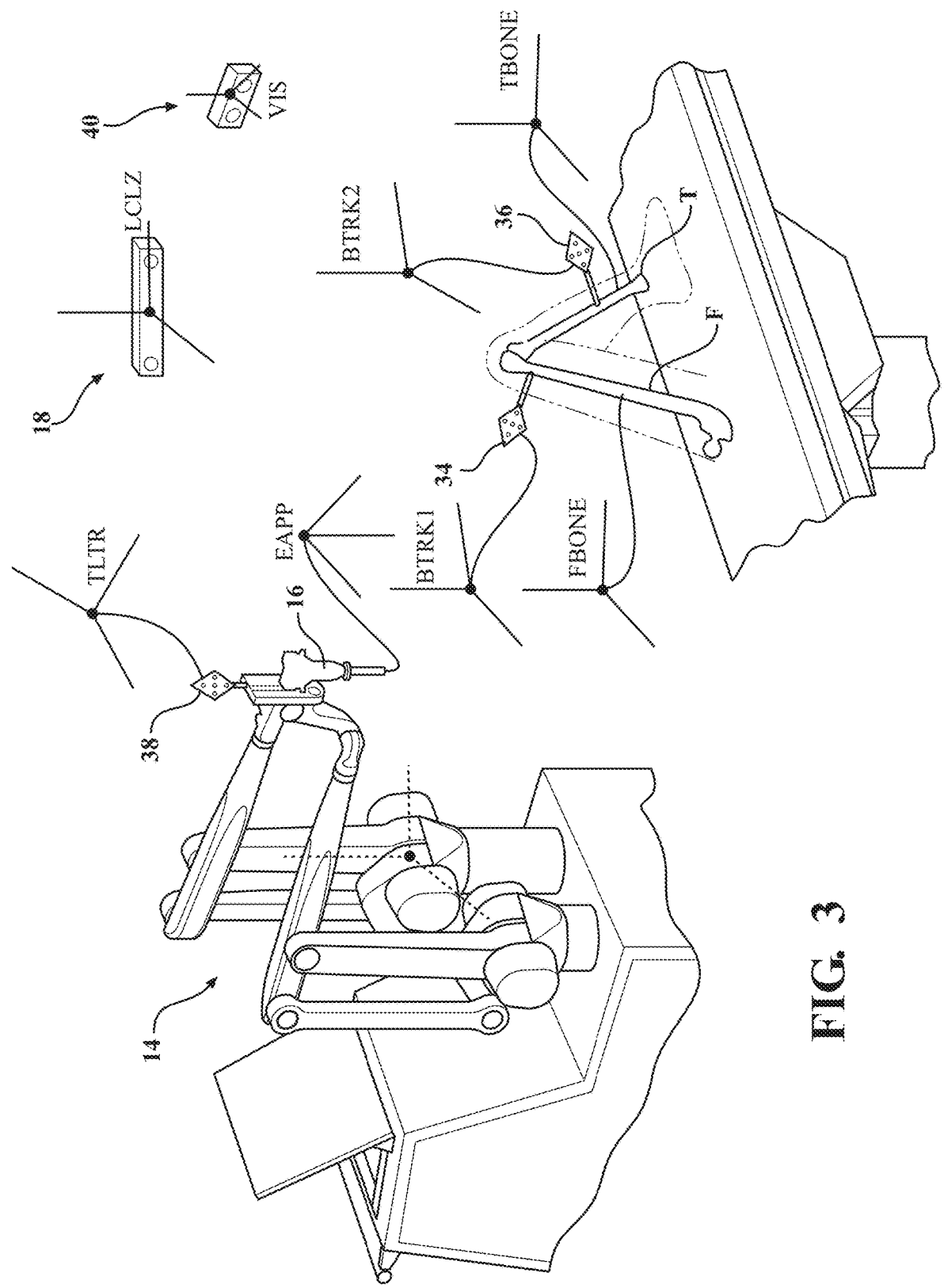
FIG. 3 is a perspective view of coordinate systems used in the surgical navigation system of FIG. 1.

FIG. 3 illustrates coordinate systems of the various objects and devices used with the surgical system 10. The navigation controller 22, such as via the transformation engine 78, may be configured transform a position of an object in one coordinate system to a position of the object in another coordinate system, such as based on positional relationships defined in the transformation data 83 stored in the navigation controller 22. Such transformations may enable the navigation controller 22 to track objects in the surgical system 10 relative to a common coordinate system. Moreover, the transformations may enable the navigation controller 22, such as via the vision engine 80, to calculate an expected depth map to be generated by the vision device 40 based on localization data generated by the localization engine 76, and to identify and track objects based on a comparison between an actual depth map generated by the vision device 40 and the expected depth map. As one non-limiting example, each of the positional relationships defined by the transformation data 83 and enabling the transformations between coordinate systems may be represented by a transformation matrix defined by the transformation data 83.

The navigation controller 22 may be configured to track objects in the target site, such as objects in the target site affixed to the trackers 34, 36, 38, with reference to a localizer coordinate system LCLZ. The localizer coordinate system LCLZ may include an origin and orientation, which may be defined by the position of the x, y, and z axes relative to the surgical workspace. The localizer coordinate system LCLZ may be fixed to and centered on the localizer 18. Specifically, a center point of the localizer 18 may define the origin of the localizer coordinate system LCLZ. The localizer data, which as described above may indicate the positions of objects relative to the localizer 18 determined using the localizer 18, may similarly indicate the positions of such objects in the localizer coordinate system LCLZ.

During the procedure, one goal is to keep the localizer coordinate system LCLZ in a known position. An accelerometer may be mounted to the localizer 18 to detect sudden or unexpected movements of the localizer coordinate system LCLZ, as may occur when the localizer 18 is inadvertently bumped by surgical personnel. Responsive to a detected movement of the localizer coordinate LCLZ, the navigation controller 22 may be configured, such as via the surgical navigator 81, to present an alert to surgical personal through the user interface 24, to halt surgical navigation, and/or to communicate a signal to the manipulator controller 50 that causes the manipulator controller 50 to halt movement of the surgical instrument 16 until the surgical system 10 is recalibrated.

Each object tracked by the surgical system 10 may also have its own coordinate system that is fixed to and centered on the object, and that is separate from the localizer coordinate system LCLZ. For instance, the trackers 34, 36, 38 may be fixed and centered within a bone tracker coordinate system BTRK1, bone tracker coordinate system BTRK2, and instrument tracker coordinate system TLTR respectively. The femur F of the patient may be fixed and centered within the femur coordinate system FBONE, and the tibia T of the patient may be fixed and centered within the tibia coordinate system TBONE. Prior to the surgical procedure, the pre-operative images and/or the virtual models for each tracked object, such as the femur F, tibia T, and surgical instrument 16, may be mapped to the object, such as by being mapped to and fixed within the coordinate system for the object in accordance with the fixed position of the object in the coordinate system.

During an initial phase of a surgical procedure, the trackers 34, 36 may be firmly affixed to the femur F and tibia T of the patient respectively. The position of coordinate systems FBONE and TBONE may then be mapped to the coordinate systems BTRK1 and BTRK2, respectively. For instance, a pointer instrument P (FIG. 1), such as disclosed in U.S. Pat. No. 7,725,162 to Malackowski et al., hereby incorporated by reference, having its own tracker PT, may be used to register the femur coordinate system FBONE and tibia coordinate system TBONE to the bone tracker coordinate systems BTRK1 and BTRK2, respectively. The fixed positional relationship between the femur coordinate system FBONE and the bone tracker coordinate system BTRK1, and the fixed positional relationship between the tibia coordinate system TBONE and the bone tracker coordinate system BTRK2, may be stored on the navigation controller 22 as transformation data 83.

Given the fixed spatial relationships between the femur F and tibia T and their trackers 34, 36, the navigation controller 22, such as via the transformation engine 78, may transform the position of the femur F in the femur coordinate system FBONE a position of the femur F in the bone tracker coordinate system BTRK1, and may transform the position of the tibia T in the tibia coordinate system TBONE to a position of the tibia T in the bone tracker coordinate system BTRK2. Thus, by determining the position of the trackers 34, 36 in the localization coordinate system LCLZ using the localizer 18, the navigation controller 22 may determine a position of the femur coordinate system FBONE and a position of the tibia coordinate system TBONE in the localization coordinate system LCLZ respectively, and may correspondingly determine a position of the femur F and tibia T in the localization coordinate system LCLZ respectively.

Similarly, the treatment end of the surgical instrument 16 may be fixed and centered within it's the coordinate system EAPP. The origin of the coordinate system EAPP may be fixed to a centroid of a surgical cutting bur, for example. The position of coordinate system EAPP, and correspondingly of the treatment end of the surgical instrument 16, may be fixed within the instrument tracker coordinate system TLTR of the tracker 38 before the procedure begins. The fixed positional relationship between the coordinate system EAPP and the instrument tracker coordinate system TLTR may also be stored in the navigation controller 22 as transformation data 83. Thus, by determining the position of the instrument tracker coordinate system TLTR in the localization coordinate system LCLZ using the localizer 18, the navigation controller 22, such as via the transformation engine 78, may determine a position of the coordinate system EAPP in the localization coordinate system LCLZ based on the positional relationship between the instrument tracker coordinate system TLTR and the coordinate system EAAP, and may correspondingly determine a position of the treatment end of the surgical instrument 16 in the localization coordinate system LCLZ.

The vision device 40 may likewise be fixed and centered within vision coordinate system VIS. The origin of vision coordinate system VIS may represent a centroid of the vision device 40. Each actual depth map generated by the vision device 40, which as described above may indicate positions of exposed surfaces in the target site relative to the vision device 40, may similarly indicate the positions of the exposed surfaces in the coordinate system VIS.

When the vision device 40 is integrated with the localizer 18, such as illustrated in FIG. 1, the vision coordinate system VIS and localizer coordinate system LCLZ may be considered equivalent. In other words, a position of an object or coordinate system in the localizer coordinate system LCLZ may be so close or equal to the position of the object or coordinate system in the vision coordinate system VIS that no transformation is needed. Alternatively, because the vision coordinate system VIS may be fixed within the localizer coordinate system LCLZ when the vision device 40 is integrated with the localizer 18, and vice versa, the positional relationship between the vision coordinate system VIS and localizer coordinate system LCLZ, and correspondingly between the vision device 40 and the localizer 18, may be determined during manufacturer of the surgical system 10, and may be factory-stored in the navigation controller 22 as transformation data 83.

When the vision device 40 is separate from the localizer 18, the vision device 40 may include a tracker (not shown) rigidly mounted to the housing of the vision device 40 to establish the positional relationship between the vision coordinate system VIS and the localizer coordinate system LCLZ, and correspondingly between the vision device 40 and the localizer 18. The navigation controller 22 may be preloaded with the positional relationship between the tracker's coordinate system and the vision coordinate system VIS as transformation data 83. Thus, by determining the position of the tracker's coordinate system in the localization coordinate system LCLZ using the localizer 18, the navigation controller 22 may determine a position of the vision coordinate system VIS in the localization coordinate system LCLZ based on the stored positional relationship between the tracker's coordinate system and the vision coordinate system VIS, and correspondingly, may determine the position of the vision device 40 in the localizer coordinate system LCLZ. Further correspondingly, the navigation controller 22 may determine the position of the vision device 40 relative to the localizer 18 in the localizer coordinate system LCLZ and the vision coordinate system VIS.

Alternatively, the navigation controller 22 may be configured to identify the positional relationship between the localizer common coordinate system LCLZ and the vision coordinate system VIS based on a common light pattern inserted into the target site and detectable by both the localizer 18 and vision device 40. For example, after the localizer 18 and vision device 40 are positioned with a field of view of the target site, a pattern of light, such as non-visible light, may be projected onto the target site, which may reflect back the pattern of light to the localizer 18 and vision device 40. The navigation controller 22 may cause the light source 44 of the vision device 40 to project this light pattern into the target site, or a separate light projector (not shown) may be used to project the light pattern. As a further example, a tracker or other physical device, such as the pointer PT (FIG. 1), having markers configured to transmit a pattern of light detectable by the localizer 18 and the vision device 40 may be placed within the target site and in the fields of views of the localizer 18 and vision device 40.

The navigation controller 22, such as via the localizer engine 76 and using the localizer 18, may be configured to generate localization data indicating the position of the light pattern in the localizer coordinate system LCLZ specific to the localizer 18. The navigation controller 22 may also receive a calibration depth map illustrating the light pattern from the vision device 40, and may be configured, such as via the transformation engine 78, to identify a position of the light pattern in the vision coordinate system VIS based on the calibration depth map. The navigation controller 22 may then be configured, such as via the transformation engine 78, to determine the positional relationship between the localization coordinate system LCLZ and the vision coordinate system LCLZ based on the determined position of the projected pattern in the localization coordinate system LCLZ and the vision coordinate system LCLZ, such as using regression algorithm.

Figure 4:
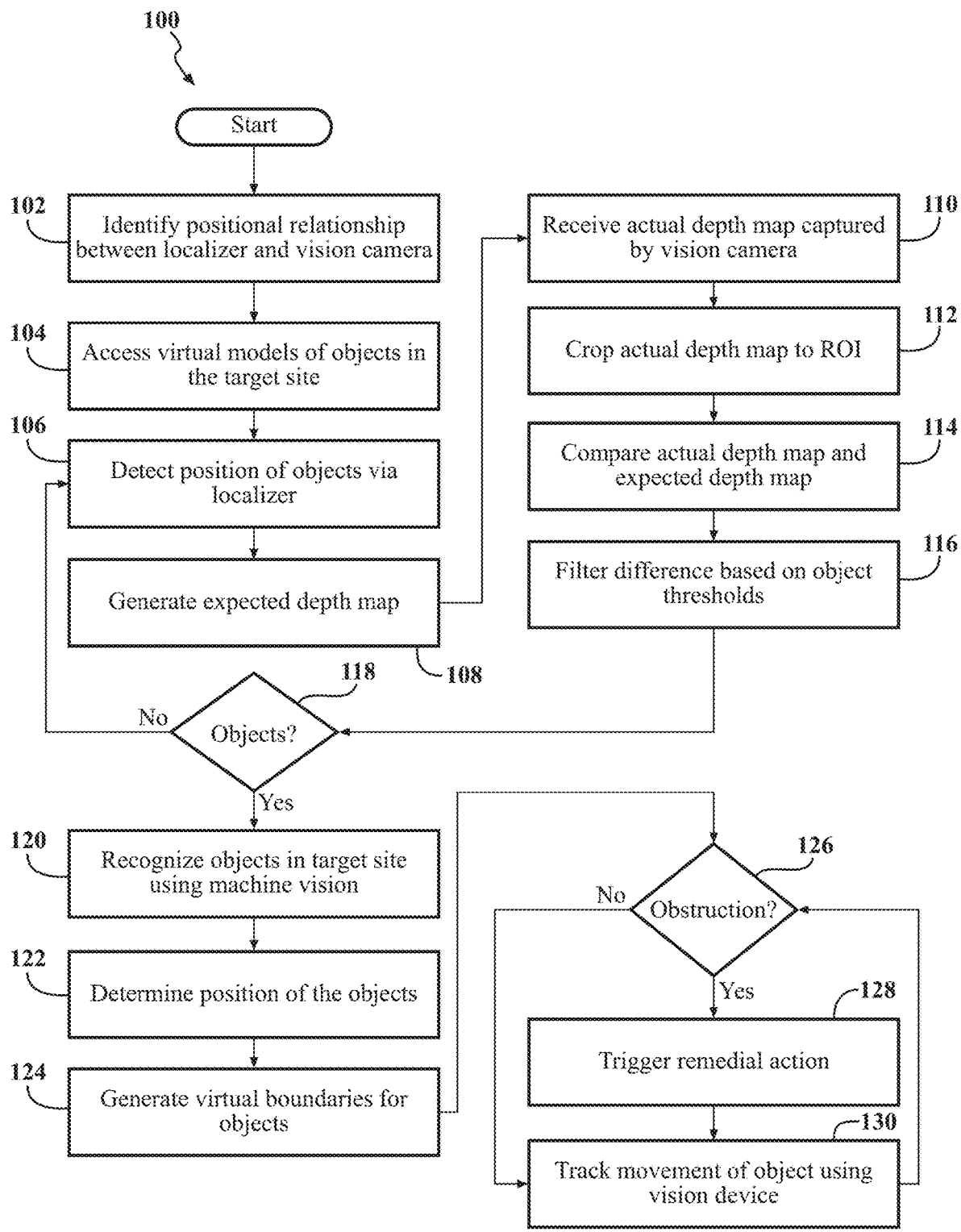
FIG. 4 is a flow chart of a method for navigating one example of a target site using tracker-based localization and machine vision.

FIG. 4 illustrates a method 100 for tracking objects in a surgical workspace and determining whether an object obstructs a surgical plan using tracker-based localization and machine vision. The method 100 may be performed by the surgical navigation system 12, or more particularly by the navigation controller 22.

In block 102, a positional relationship between the localizer 18 and the vision device 40 in a common coordinate system may be identified. Specifically, the navigation controller 22, such as via the transformation engine 78, may be configured to identify the positional relationship between the localizer 18 and the vision device 40, and correspondingly between the localizer coordinate system LCLZ and vision coordinate system VIS, using any of the methods described above. For example, a tracker may be fixed to the vision device 40, or a light pattern may be placed in the target site that is detectable by both the localizer 18 and the vision device 40. Alternatively, when the localizer 18 is integrated with or otherwise fixed relative to the vision device 40 during manufacture, the positional relationship may be determined and pre-stored as transformation data 83 in the navigation controller 22 during manufacture.

In block 104, a virtual model corresponding to one or more objects in the target site may be accessed, such as based on the transformation data 83. The transformation data 83 may indicate objects in the target site to which trackers, such as the trackers 34, 36, 38, are affixed. The navigation controller 22 may be configured to retrieve the virtual models for each of the objects affixed to a tracker. In some instances, one or more of these retrieved virtual models may also define a target volume to be treated during the surgical procedure.

Figure 5:
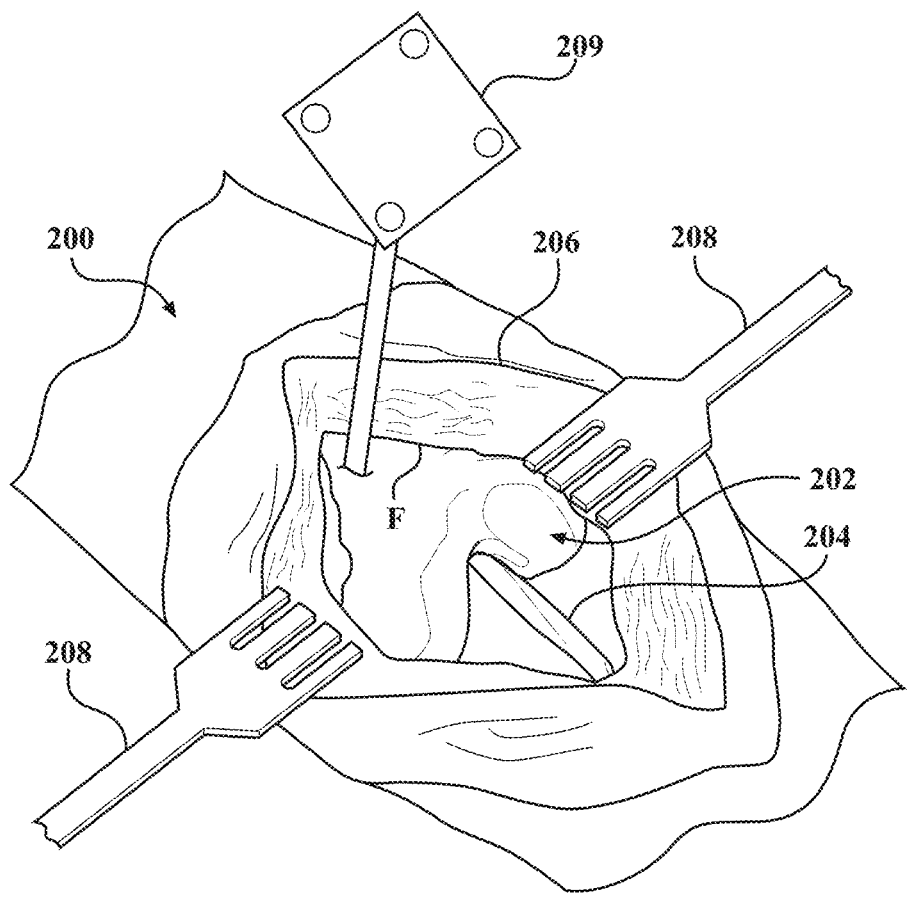
FIG. 5 is an illustration of one example of a target site, e.g., an anatomy being treated during a surgical procedure.

FIG. 5 illustrates a target site 200 of a patient undergoing a knee replacement procedure. The target site 200 may include a portion of the patient's femur F, which may contain a target volume 202 of bone tissue to be removed with a surgical instrument (e.g., the surgical instrument 16). The target site 200 may further include soft tissue adjacent the target volume 202, such as a ligament 204 and epidermal tissue 206. The target site 200 may also include surgical tools, such as retractors 208 positioned to retract the epidermal tissue 206 and provide access to the patient's femur F. The target site 200 may additionally include a tracker 209 firmly affixed to the patient's femur F. The navigation controller 22 may therefore retrieve a virtual model corresponding to the femur F from the model data 82, an example of which is illustrated in FIG. 6.

Referring again to FIG. 4, in block 106, the positions of objects affixed to trackers in the target site may be detected using the localizer 18. In particular, the localizer 18 may be configured to generate optical-based data indicating the position of each tracker coordinate system, and correspondingly the position of each tracker, in the localizer coordinate system LCLZ as described above. The navigation controller 22 may then be configured, such as via the localization engine 76, to identify positions of the coordinate systems of the objects affixed to the trackers, and correspondingly the positions of the objects, in the localizer coordinate system LCLZ, such as based on the detected positions of the trackers and their coordinate systems, and the positional relationships between the trackers and the objects indicated in the transformation data 83. Because the virtual model for each object affixed to a tracker may be mapped to the object's coordinate system in the transformation data 83, the navigation controller 22 may similarly identify a position of the virtual model for each object affixed to a tracker in the localizer coordinate system LCLZ based on the detected position of the tracker to which the object is affixed and the positional relationship between the tracker and the object.

Figure 6:
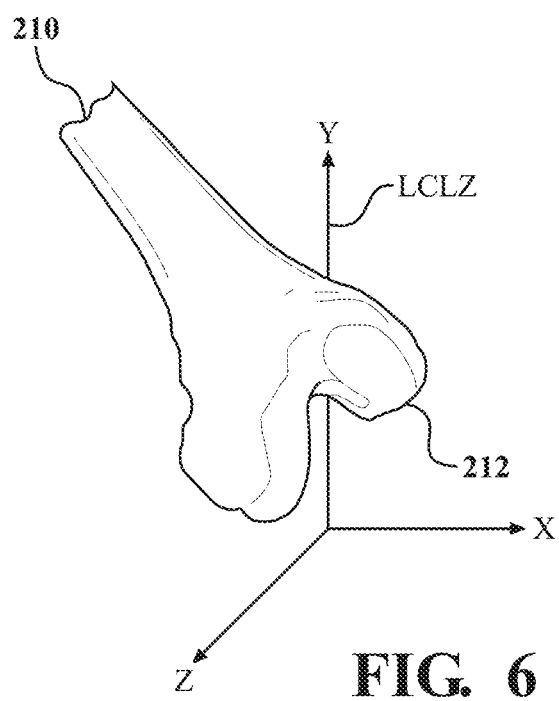
FIG. 6 is an illustration of a position of a virtual model corresponding to an object in the target site of FIG. 5.

FIG. 6 illustrates a continuation of the target site 200 of FIG. 5 and shows a virtual model 210 that may correspond to the patient's femur F, which may be affixed to the tracker 209 in the target site 200. The virtual model 210 may be positioned in the localizer coordinate system LCLZ according to the position of the tracker 209 and femur F in the localizer coordinate system LCLZ determined with the localizer 18. The virtual model 210 may define a virtual target volume 212 to be removed from the femur F during treatment, which may correspond to the target volume 202 shown in FIG. 5.

In block 108, an expected depth map be generated, such as based on the accessed virtual models, the detected positions of the objects corresponding to the virtual models in the localizer coordinate system LCLZ, and the positional relationship between the localizer 18 and the vision device 40 in the common coordinate system. As previously described, the positions of the virtual models in the localizer coordinate system LCLZ may correspond to the positions of the objects in the localizer coordinate system LCLZ determined using the localizer 18. The navigation controller 22 may be configured, such as via the vision engine 80, to transform the positions of the virtual models in the localizer coordinate system LCLZ to positions of the virtual models in the vision coordinate system VIS based on the positional relationship between the localizer 18 and the vision device 40, and correspondingly between the localizer coordinate system LCLZ and the vision coordinate system VIS, in the common coordinate system.

Thereafter, the navigation controller 22 may generate an expected depth map based on the positions of the virtual models in the vision coordinate system VIS. As described above, a depth map generated by the vision device 40 may illustrate the position (e.g., depth and location) of exposed object surfaces in the target site relative to the vision device 40. The position of the virtual models in the vision coordinate system VIS may summarily indicate the position of object surfaces represented by the virtual models relative to the vision device 40, which may be fixed within the vision coordinate system VIS. Accordingly, the navigation controller 22 may be configured, such as via the vision engine 80, to simulate a depth map expected to be generated by the vision device 40 with a field of view of the target site based on the determined positions of the virtual models in the vision coordinate system VIS, assuming the target site is free of any other objects.

Figure 7:
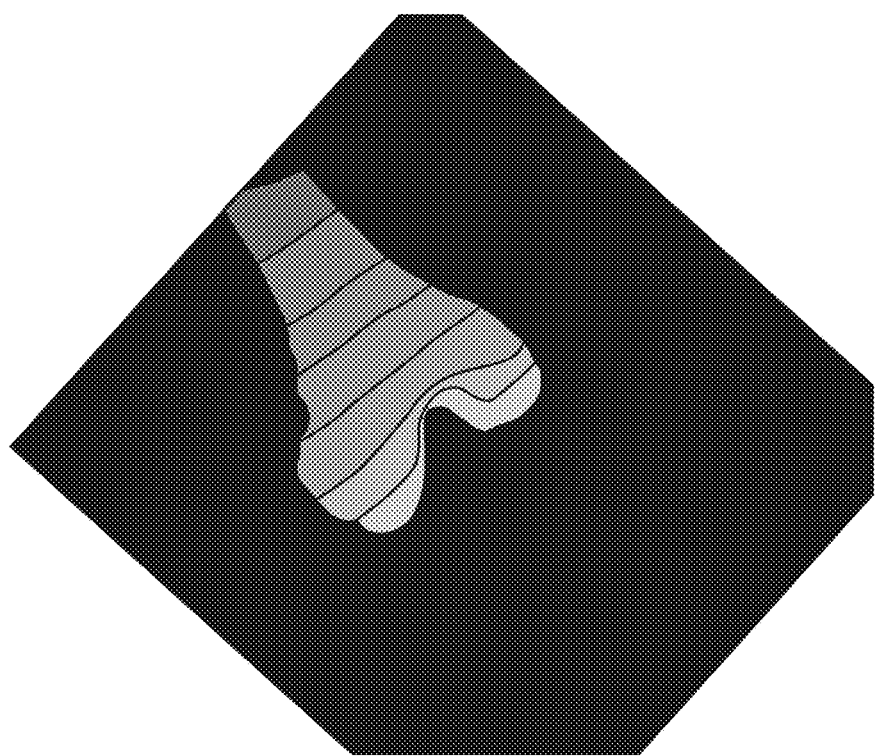
FIG. 7 is an illustration of an expected depth map based on the virtual model of FIG. 6.

FIG. 7 illustrates an expected depth map that may be generated based on the virtual model 210 of FIG. 6. The expected depth map of FIG. 7 may simulate the depth map expected to be generated by the vision device 40 of patient's femur F according to the transformed position of the virtual model 210 in the vision coordinate system VIS, assuming other objects, such as the ligament 204, epidermal tissue 206, retractors 208, and tracker 209 are absent from the target site. The expected depth map of FIG. 7 may also have been cropped to a region of interest, discussed in more detail below.

In block 110, an actual depth map captured by the vision device 40 may be received. In particular, contemporaneously with the localizer 18 generating localizer data indicating the positions of objects affixed to trackers in the target site in block 106, the vision device 40 may generate a depth map of the target site as described above. In this way, the depth map may be temporally interleaved with the localization data, and may also be temporally interleaved with the estimated depth map generated based on the localization data. In other words, the actual depth map and the expected depth map may both represent the target site at a substantially same moment in time during a surgical procedure.

Figure 8:
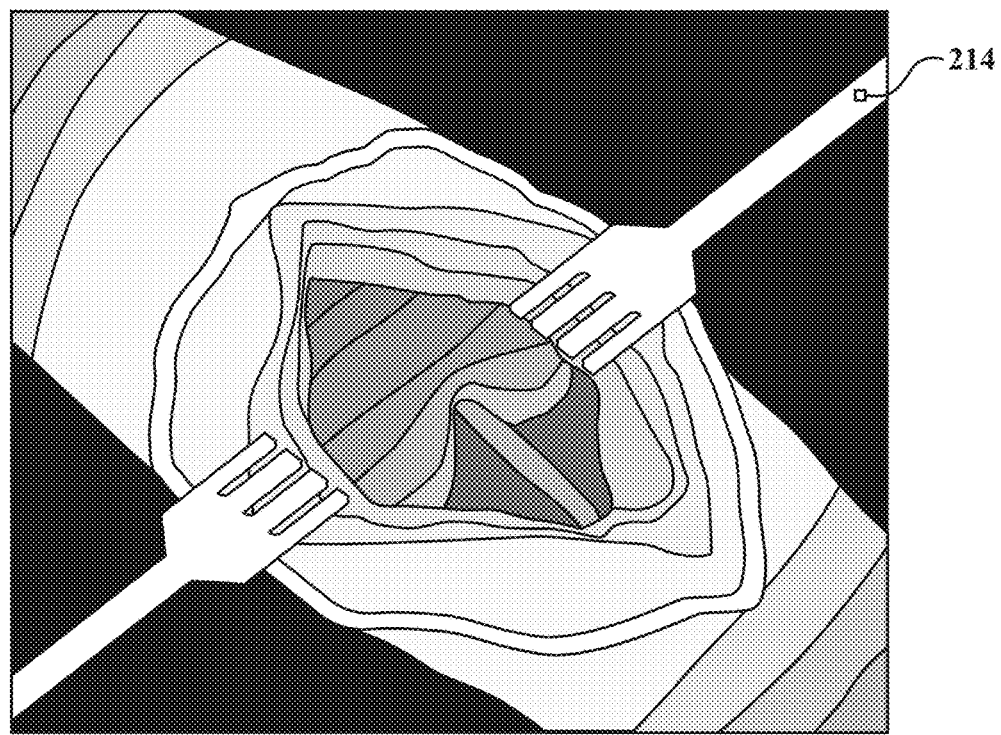
FIG. 8 is an illustration of an actual depth map captured by the vision device of FIG. 1.

FIG. 8 illustrates a depth map that may be generated by the vision device 40 with a field of view the target site 200 depicted in FIG. 5, with the tracker 209 removed for simplicity. The depth map may include several image components, akin to pixels, arranged as a matrix and forming the image frame of the depth map. A box 214 has been artificially placed on the illustrated depth map to highlight an example one of the image components. The location of each image component in the depth map image frame may represent a horizontal and vertical distance from a center viewpoint of the vision device 40, and the brightness of each image component may correspond to the distance of the object surface point represented by the image component from the vision device 40. In the illustrated example, brighter image components represent surface points in the target site that are closer to the vision device 40, and darker image components represent surface pints in the target site that are farther from the vision device 40.

In block 112, the actual depth map may be cropped to a region of interest (ROI) for the surgical procedure, such as based on the virtual models accessed in block 104, the detected positions of the objects corresponding to the virtual models in the localizer coordinate system LCLZ, and the positional relationship between the localizer 18 and vision device 40 in the common coordinate system. As explained in further detail below, the actual depth map may be compared with the expected depth map to identify objects in the target site and to determine whether any such objects may obstruct treatment of a target volume in the target site. The larger the dimensions of the actual depth map and the expected depth map being compared, the greater amount of computations involved in the comparison. The navigation controller 22, such as via the vision engine 80, may thus be configured to crop the actual depth map to an ROI based on the positions of the virtual models in the vision coordinate system VIS to reduce the dimensions of the compared depth images. As described above, the position of the virtual models in the vision coordinate system VIS may be determined based on the determined position of the objects localizer coordinate system LCLZ and the positional relationship between the localizer 18 and the vision device 40 in the common coordinate system.

For example, the virtual models accessed in block 104 may define a target volume to be treated during the surgical procedure. The position of the virtual models in the vision coordinate system VIS may thus indicate the position of the target volume in the vision coordinate system VIS, and correspondingly, may indicate the position of the target volume in the actual depth map generated by the vision device 40. The navigation controller 22, such as via the vision engine 80, may be configured to crop the actual depth map to remove any areas greater than a threshold distance from the position of the target volume in the vision coordinate system VIS. Additionally or alternatively, the navigation controller 22, such as via the vision engine 80, may be configured to center a user-selected or procedure-specific shape on the position of the target volume in the actual depth map, and to remove any areas of the actual depth map outside of the shape. The navigation controller 22 may be configured to limit the dimensions and shape of the expected depth map to the dimensions and shape of the cropped actual depth map, such as during or after calculation of the expected depth map.

Figure 9:
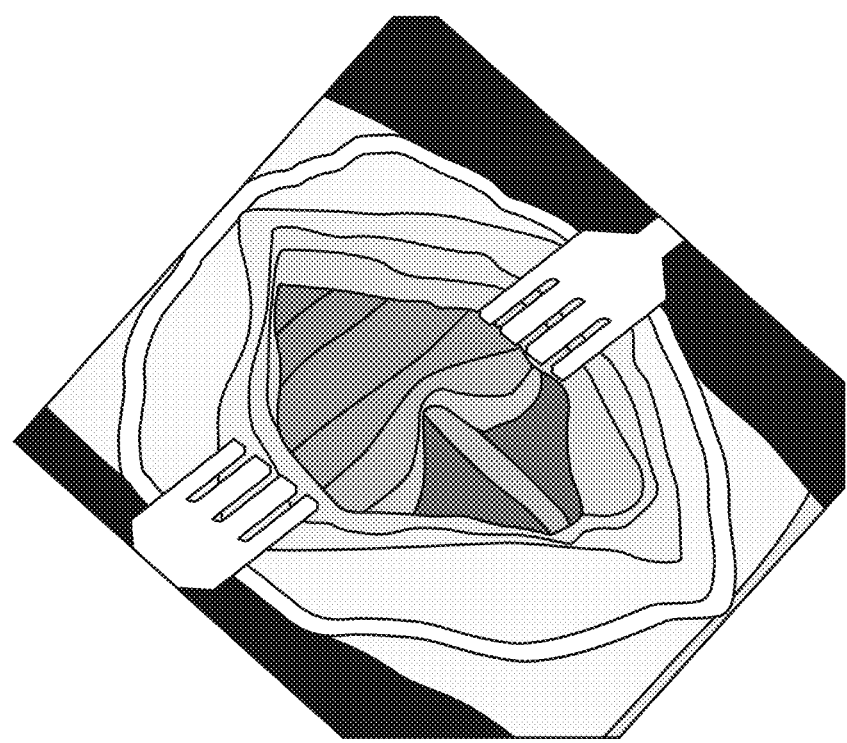
FIG. 9 is an illustration of the actual depth map of FIG. 8 cropped to a region of interest.

FIG. 9 illustrates the actual depth map of FIG. 8 cropped to an ROI based on the virtual model 210 corresponding to the femur F in FIG. 6. The virtual model 210 may define a virtual target volume 212 corresponding to the target volume 202 to be treated during the surgical procedure. The navigation controller 22 may crop the actual depth map of FIG. 8 based on the determined position of the target volume in the vision coordinate system VIS, which may indicate the position of target volume in the actual depth map, such as by centering a selected shape on the target volume in the depth map and removing areas of the depth map outside of the shape. The expected depth map of FIG. 7 is similarly limited to the dimensions and shape of the cropped actual depth map.

In blocks 114 and 116, a portion of the depth map that fails to match the expected depth map be identified. Specifically, in block 114, the actual depth map may be compared with the expected depth map, such as by computing a difference between the actual depth map and the expected depth map. The navigation controller 22 may be configured, such as via the vision engine 80, to compute the difference between the expected depth map and the actual depth by computing a difference between the depths at each corresponding pair of image components in the expected depth map and the actual depth map. A corresponding pair of image components in the expected depth map and the actual depth map may include the image component of each depth map at a same horizontal and vertical location. Assuming the actual depth map has been cropped to an ROI in block 112, the depth maps compared in block 114 may be the cropped depth map.

Figure 10:
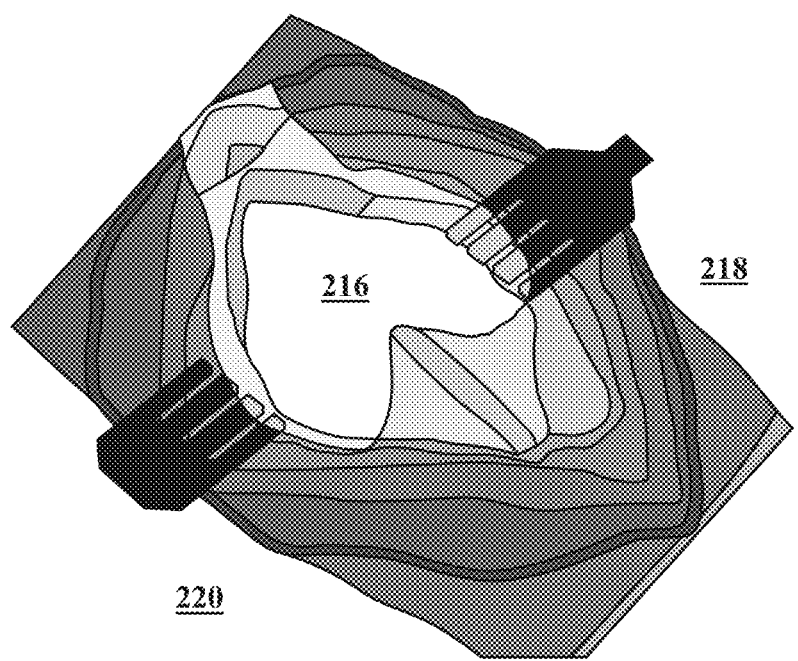
FIG. 10 is an illustration of the difference between the expected depth map of FIG. 7 and the actual depth map of FIG. 9.

The difference between the actual depth map and estimated depth may indicate objects in the target site that are not already identified and tracked, such as objects (e.g., soft tissue, surgeon's hand) that are not or cannot be adequately tracked using an affixed tracker. The difference may be represented by a difference depth map, with each image component of the difference depth map indicating the depth difference computed for corresponding image components located in the actual and expected depth maps at a same horizontal and vertical position as the image component in the difference depth map. FIG. 10 illustrates a difference depth map computed between the actual depth map of FIG. 9 and the expected depth map of FIG. 7.

Corresponding image components from the actual depth map and expected depth map that indicate a same depth will result in a zero depth difference, and may correspond to objects previously identified and tracked, such as using trackers and the localizer 18. A zero depth difference may be represented in a depth map for the difference by image components with a maximum brightness or a color and/or hue specific to zero depth. In the difference depth map of FIG. 10, the areas 216, 218, and 220 represent corresponding image components from the actual depth map and expected depth map with a zero depth difference.

Corresponding image components of the actual depth map and the expected depth map that do not indicate a same depth will result in a non-zero depth difference, and may correspond to objects not previously identified and tracked, such as using the trackers and localizer 18. A non-zero depth difference may be represented in a depth map for the difference with image components of a brightness that is less than maximum brightness, or a color that differs from the color and/or hue specific to zero depth. In the difference depth map of FIG. 10, the darker areas adjacent the areas 216, 218, and 210 represent corresponding image components of the actual depth map and expected depth map with a non-zero depth difference.

In block 116, the computed difference may be filtered based on one or more object thresholds. The object thresholds may be designed to differentiate between non-zero differences that are due to noise or inconsequential calibration inaccuracies and non-zero differences that are due to the presence of additional objects in the target site. The object thresholds may include without limitation a threshold depth and/or a minimum size threshold, each of which may be non-zero.

As an example, for each of one or more non-zero sections of the difference depth map, the navigation controller 22 may be configured to determine whether the non-zero section indicates an absolute depth greater than the depth threshold. Specifically, the difference depth map may include one or more non-zero sections, each of the non-zero sections including a set of contiguous image components that each indicate a non-zero depth difference. A non-zero section of the difference depth map may be considered to have an absolute depth greater than the depth threshold if the magnitude (without reference to sign) of the non-zero depth difference indicated by each image component in the non-zero section is greater than the depth threshold. Responsive to determining that a non-zero section of the difference indicates an absolute depth greater than the threshold depth, the navigation controller 22 may be configured to identify as a portion of the actual depth map that fails to match the estimated depth map the section of the actual depth map that corresponds the non-zero section of the difference, such as by virtue of the section of the actual depth map being at a same horizontal and vertical position in the actual depth map as the non-zero section in the difference depth map.

As a further example, for each non-zero section of the difference, the navigation controller 22 may be configured to determine whether a size (e.g., area) of the non-zero section is greater than the minimum size threshold. Responsive to determining that the size of a non-zero section is greater than the minimum size threshold, the navigation controller 22 may be configured, such as vis the vision engine 80, to identify as a portion of the actual depth map that fails to match the expected depth map the section of the actual depth map that corresponds the non-zero section of the difference, such as by virtue of the section of the actual depth map being at a same horizontal and vertical position in the actual depth map as the non-zero section in the difference depth map.

In another example, the navigation controller 22 may be configured to identify as a portion of the actual depth map that fails to match the estimated depth map a section of the actual depth map that corresponds a non-zero section of the difference responsive to determining that the size of the non-zero section is greater than the minimum size threshold and the non-zero section indicates an absolute depth greater than the threshold depth.

In block 118, a determination may be made of whether objects are present in the target site based on filtered difference. Specifically, the navigation controller 22, such as via the vision engine 80, may be configured to determine whether any portions of the actual depth map that do not match the expected depth map were identified. If not ("No" branch of block 118), then the method 100 may return to block 106 to again detect the position of tracker-affixed objects using the localizer 18. If so ("Yes" branch of block 118), then the method 100 may proceed to block 120 to recognize objects in the target site by applying machine vision techniques to the portion of the actual depth map that fails to match the expected depth map.

In block 120, the navigation controller 22, such as via the vision engine 80, may be configured to apply machine vision techniques to the identified portion of the actual depth map that fails to match the expected depth map to recognize objects in target site from the identified portion. For instance and without limitation, the navigation controller 22 may be configured utilize pattern recognition, edge detection, color recognition, wavelength analysis, image component intensity analysis (e.g., pixel or voxel intensity analysis), depth analysis, and metrics generated through machine learning to segment between objects represented in the identified portion of the actual depth map. As some examples, areas of the identified portion separated by edges, having different regular patterns, having different color pallets, and/or indicating different depth ranges may correspond to different objects. As further examples, the surfaces of different objects (e.g., different tissues) in the target site may produce different wavelengths and/or different intensities in the signals reflected to and detected by the vision device 40. The vision device 40 may be configured to output such information for each image component of the actual depth map, and based on this information, the navigation controller 22 may be configured to segment different objects in the identified portion based on varying wavelengths and/or signal intensities occurring across the identified portion of the actual depth map. If the navigation controller 22 is unable discover multiple objects in the identified portion using machine vision, then the navigation controller 22 may be configured to consider the entire identified portion as single object in the target site.

Additionally, or alternatively, the navigation controller 22 may be configured, such as via the vision engine 80, to identify objects in the identified portion of the actual depth, such as based on the model data 82 stored in the navigation controller 22. Identification may differ from segmentation in that identification may identify a label for each object represented in the actual depth map describing the type of object, such as identifying the object as a ligament, retractor, epidermal tissue, and so on. Identification of each object in the target site may enable the navigation controller 22, such as via the vision engine 80, to model the entire object as opposed to just a surface of the object, and to better predict movement and other reactions of the object during the surgical procedure, which may enable the surgical navigator 81 of the navigation controller 22 to make increasingly informed navigation decisions.

As described above, the model data 82 stored in the navigation controller 22 may define three-dimensional models corresponding to objects potentially present in the target site. The model data 82 may also define predetermined profiles for various objects potentially present in the target site, each profile setting forth one or more features specific to the object that aid the navigation controller 22 in identifying the object from the actual depth map. For example, a profile for a given object may include, without limitation, one or more of a color palate, wavelength range, signal intensity range, distance or depth range, area, volume, shape, polarization, and deep metrics output from a learned or statistical model corresponding to the object. The profile for a given object may also include a three-dimensional model for the object, such as one generated from patient scans described above.

The navigation controller 22 may thus be configured to identify an object based on the identified portion of the actual depth map that fails to match the estimated depth map by matching at least part of the identified portion with one of the predefined profiles, namely, the predefined profile corresponding to the object. The navigation controller 22 may then be configured to label the at least part of the identified potion of the actual depth map as the specific object corresponding to the profile, which may then be considered adjacent to the localizer objects.

In an alternative example, a user may interact with the user interface 24 to manually select an object of the identified portion segmented by the navigation controller 22, and/or to select a predefined profile for the selected object. A user may also interact with the user interface 24 to manually trace an object represented by the actual depot map, such as in the identified portion, and/or to select a predefined profile for the traced object. The navigation controller 22 may then be configured to label the selected segmented or traced object with the label corresponding to the selected predefined profile, and to track the selected or traced object accordingly.

In block 122, a position of each object recognized from the actual depth map may be determined in a common coordinate system with the localized objects, such as the vision coordinate system VIS or the localizer coordinate system LCLZ. For example, the navigation controller 22, such as via the vision engine 80, may be configured to determine the position of each object recognized from the depth map and of each localized object in the common coordinate system relative to a target volume, which may be defined by the localized objects, so that the navigation controller 22 may determine whether any of the recognized objects and/or localized objects pose an obstacle to treating the target volume.

The navigation controller 22 may be configured to determine the position each recognized object relative to the localized objects based on the detected locations of the localized objects in the localizer coordinate system LCLZ using the localizer 18, a location of the recognized object in the actual depth map, and the positional relationship between the localizer 18 and the vision device 40 in the common coordinate system, which may be defined by the transformation data 83 stored in the navigation controller 22. As previously described, the position of the recognized object in the actual depth map may indicate the position of the recognized object in the vision coordinate system VIS. For instance, each image component of the actual depth map that forms the recognized object may represent a vector from a center viewpoint of the vision device 40 to a position in the vision coordinate system VIS. The position of each image component in the image frame of the actual depth map may indicate the horizontal and vertical components of the vector, and depth indicated by each image component may represent the depth component of the vector.

The navigation controller 22 may thus be configured to determine the position of each recognized object in the vision component system VIS based on the position of the object in the actual depth map, and may then be configured to determine the position of each recognized object relative to the localized objects in a common coordinate system using the positional relationship between the localizer 18 and the vision device 40, the position of each recognized object in the vision coordinate system VIS, and/or the position of each localized object in the localizer coordinate system LCLZ.

In block 124, for each tracked object, including objects recognized from the actual depth map and objects localized with the localizer 18, a virtual boundary corresponding to the object may be generated in the common coordinate system, such as based on the determined position of the object in the common coordinate system. In particular, the navigation controller 22, such as via the vision engine 80, may be configured to generate the virtual boundaries in the common coordinate system to provide a constraint on motion of a surgical tool, such as the surgical instrument 16. To this end, the navigation controller 22 may also be configured to track movement of the surgical instrument 16 in the common coordinate system, such as with the localizer 18. The virtual boundaries generated by the navigation controller 22 may define areas of the common coordinate system that the surgical instrument 16 should not travel into or nearby, as the space may be occupied by other objects including sensitive anatomical structures and other surgical tools.

For example, the navigation controller 22 may be configured to insert in the common coordinate system the three-dimensional virtual model stored for each localized object in accordance with the determined position of the localized object in the common coordinate system. When the model data 82 stored in the navigation controller 22 defines a three-dimensional virtual model for a given object recognized from the identified portion of the actual depth map, the navigation controller 22 may be configured to insert the three-dimensional virtual model into the common coordinate system in accordance with the determined position of the given recognized object in the common coordinate system. Additionally, or alternatively, the model data 82 may indicate one or more primitive geometric shapes (e.g., spheres, cylinders, boxes) for a given object recognized from an identified portion of the actual depth map. In this case, the navigation controller 22 may be configured to size and/or arrange the indicated primitive geometric shapes based on the surface topography of the object indicated by the actual depth map, and to insert the sized and/or arranged primitive geometric shapes into the common coordinate system in accordance with the determined position of the given object in the common coordinate system. Additionally or alternatively, such as when no virtual model or primitive geometric shapes are indicated for a given object recognized from the identified portion of the actual depth map, the navigation controller 22 may be configured to construct a mesh boundary based on the surface topography of the object indicated in the actual depth map, and to insert the mesh boundary into the common coordinate system in accordance with the determined position of the given object in the common coordinate system.

As a further example, in addition or alternatively to one or more of the above techniques, the navigation controller 22 may be configured to approximate a boundary for a given object in the common coordinate system by inserting force particles in the common coordinate system in accordance with the determined position of the of the given object in the common coordinate system. Specifically, the navigation controller 22 may be configured to select various points on the surface of recognized object, and to place force particles in the common coordinate system at the determined positions of the various points in the common coordinate system. Each of the force particles may be configured to repel other objects that move near the force particle in the common coordinate system, such as by coming within a predetermined distance. Thus, during tracked movement of the surgical instrument 16 in the common coordinate system, the force particles may repel the surgical instrument 16, thereby preventing the surgical instrument 16 from colliding with the object represented by the force particles. Inserting force particles into the common coordinate system that correspond to various points on a recognized object's surface rather than a virtual boundary representing to the recognized object's entire surface may result in generation of a virtual boundary for the object using relatively reduced processing bandwidth and less data.

Figure 13:
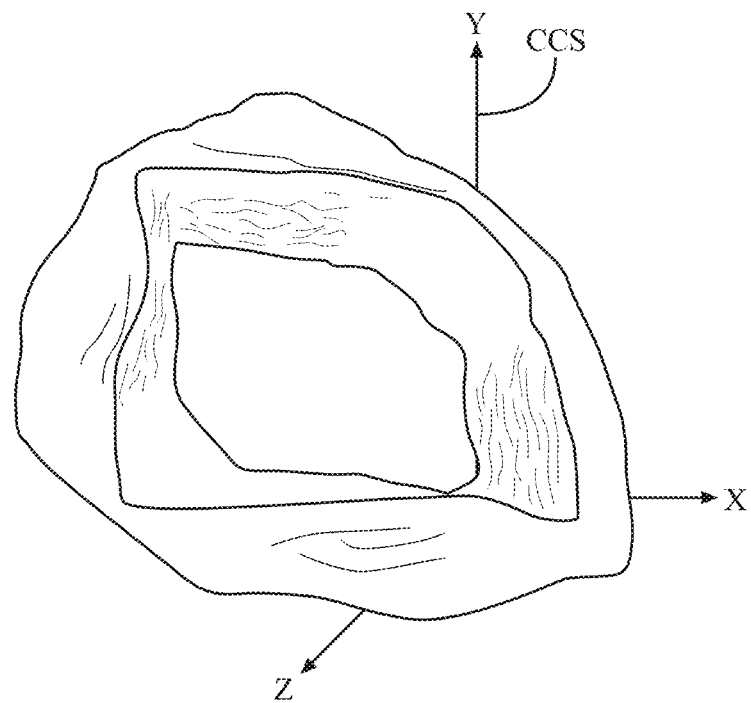
FIG. 13 is an illustration of a virtual model corresponding to epidermal tissue identified in the actual depth map of FIG. 9.

As examples, FIGS. 11 to 13 illustrate virtual boundaries in the common coordinate system that correspond to objects in the target site 200 (FIG. 5) that may have been recognized from an identified portion of the actual depth map of FIG. 9 that fails to match the expected depth map of FIG. 7 based on the difference illustrated in FIG. 10. Specifically, FIG. 11 illustrates in the common coordinate system a retractor virtual model corresponding to the retractors 208 in the target site 200 and depicted in the actual depth map, FIG. 12 illustrates in the common coordinate system a ligament virtual model corresponding to the ligament 204 in the target site 200 and depicted in the actual depth map, and FIG. 13 illustrates in the common coordinate system an epidermal tissue virtual model corresponding to the epidermal tissue 206 in the target site 200 and depicted in the actual depth map. As alternative examples, a virtual boundary for the ligament 204 in the target site 200 may be in the form of a primitive geometric object, such as a cylinder, inserted in the common coordinate system in accordance with the determined position of the ligament 204 in the common coordinate system, and a virtual boundary for the epidermal tissue 206 in the target site 200 may be in the form of a mesh surface or force particles inserted in the common coordinate system at the determined position of the epidermal tissue 206 in the common coordinate system.

Figure 14:
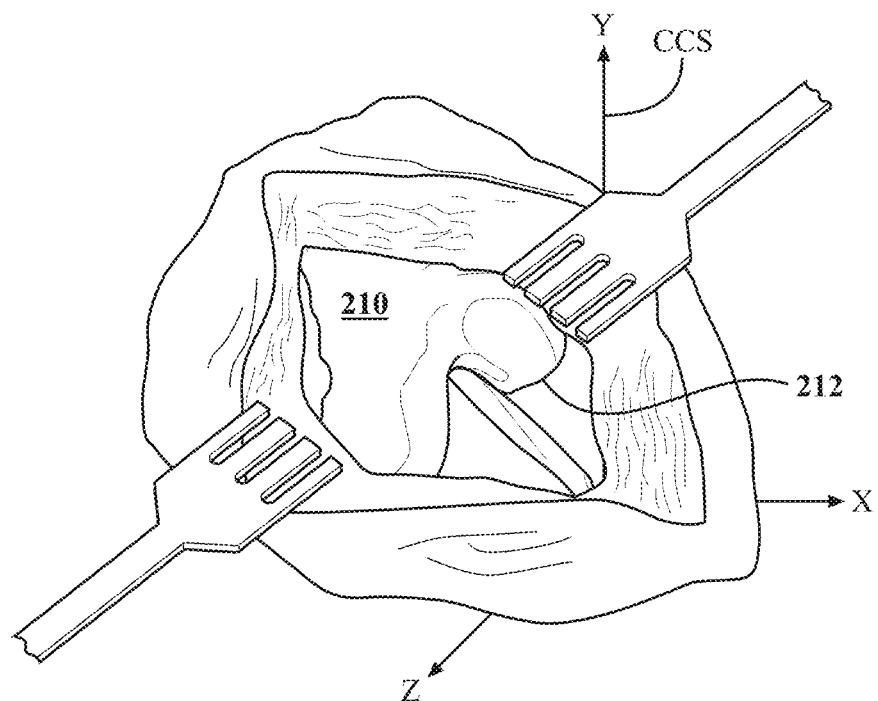
FIG. 14 is an illustration of the virtual models of FIGS. 6 and 11-13 in a common coordinate system.

FIG. 14 illustrates the relative positions of the objects recognized from the actual depth map and the patient's femur F as localized with the localizer 18 in the common coordinate system. In particular, the illustration includes the virtual models of FIGS. 11-13 and the virtual model 210 of the patient's femur F illustrated in FIG. 6. During a surgical procedure, the navigation controller 22, such as via the surgical navigator 81, may be configured to display the illustration of FIG. 14 along with an image or virtual model for the surgical instrument 16 at the current position of the surgical instrument 16 in the common coordinate system, such as tracked with the localizer 18, to aid a surgeon in guiding the surgical instrument 16 to the target volume 202.

In block 126, a determination may be made of whether a potential obstacle is present in the target site based on the tracked objects and/or the surgical plan 84. Specifically, the navigation controller 22, such as via the surgical navigator 81, may be configured to determine whether one of the tracked objects, such as the objects recognized form the actual depth map, is an obstacle to the surgical plan 84 based on the position of the object relative to the target volume in the common coordinate system and the surgical plan 84. For instance, the surgical plan 84 may define a planned trajectory of the surgical instrument 16 through the common coordinate system to treat the target volume. If the planned trajectory causes a collision with one of the virtual boundaries for the tracked objects, the navigation controller 22 may be configured to determine that an obstacle exists.

Responsive to determining that an obstacle is present ("Yes" branch of block 126), in block 128, a remedial action may be triggered. The navigation controller 22, such as via the surgical navigator 81, may be configured to trigger the remedial action by performing one or more of several available actions. As an example, responsive to determining that an object is an obstacle to the surgical plan 84, the navigation controller 22 may be configured to alter the surgical plan 84 to avoid the obstacle. For instance, the navigation controller 22 may be configured to alter the trajectory of surgical instrument 16 to avoid the obstacle, and to transmit the altered surgical plan 84 to the manipulator controller 50 for implementation. As another example, the navigation controller 22 may be configured to halt surgical guidance provided by the surgical navigation system 12 and movement of the robotic manipulator 14 until the obstacle is cleared, as detected by the navigation controller 22. The navigation controller 22 may also be configured to trigger an alarm and/or notification of the obstacle via the user interface 24 of the surgical navigation system 12. As a further example, when the object causing the obstacle is identified as soft tissue, the navigation controller 22 may be configured to provide soft tissue guidance via the user interface 24. For instance, the navigation controller 22 may be configured to illustrate a position the soft tissue object causing the obstacle relative to other objects in the target site, and provide a suggestion for moving the soft tissue to clear the obstacle. The navigation controller 22 may be configured to continue monitoring the position of the soft tissue in the common coordinate system while providing the soft tissue guidance, and provide a notification to the user when the obstacle threat is cleared.

Following the triggering and/or overcoming of a remedial action (block 128), or responsive to an obstacle not being identified ("No" branch of block 126), in block 130, movement of objects recognized from the actual depth may be tracked using the vision device 40. Specifically, the navigation controller 22, such as via the vision engine 80, may be configured to track movement of each recognized object by being configured to monitor a state of the portion of the actual depth map corresponding to the recognized object in additional actual depths maps subsequently generated by the vision device 40. By focusing on changes to the portion of the actual depth map previously determined to correspond to the recognized object in subsequently generated depth maps, as opposed to generating an expected depth map for each subsequently generated actual depth map, computing a difference between the expected depth map and the subsequent actual depth map, and matching a stored profile to the difference, the navigation controller 22 may be able to monitor movement of the recognized object with increased speed going forward.

More particularly, each portion of the actual depth map corresponding to a recognized object may depict an arrangement of features specific to the object and located in a specific position of the actual depth map. For example and without limitation, the arrangement of features may be an arrangement of vertices having a geometric relationship specific to the object, an arrangement of edges or lines having a geometric relationship specific to the object, or an arrangement of depths having a relative and geometric relationship specific to the object. Furthermore, the spatial relationship between the arrangement of features of the object and the rest of the object may be fixed.

The navigation controller 22 may thus be configured to monitor for movement of an object recognized from the actual depth map by monitoring whether the arrangement of features specific to the object in the actual depth moves to a position in the additional depth map that differs from the position of the arrangement in actual depth map. If so, then the navigation controller 22 may be configured to determine a new position of the object in the common coordinate system based on the new position of the arrangement of features corresponding to the object in the additional depth map, and to update the virtual boundary associated with the object in the common coordinate system accordingly. The arrangement of features for monitoring movement of a given object may be indicated in model data 82 for the object, or may be set manually by a user by selecting points in the portion of the actual depth map corresponding to the object using the user interface 24.

Figure 15:
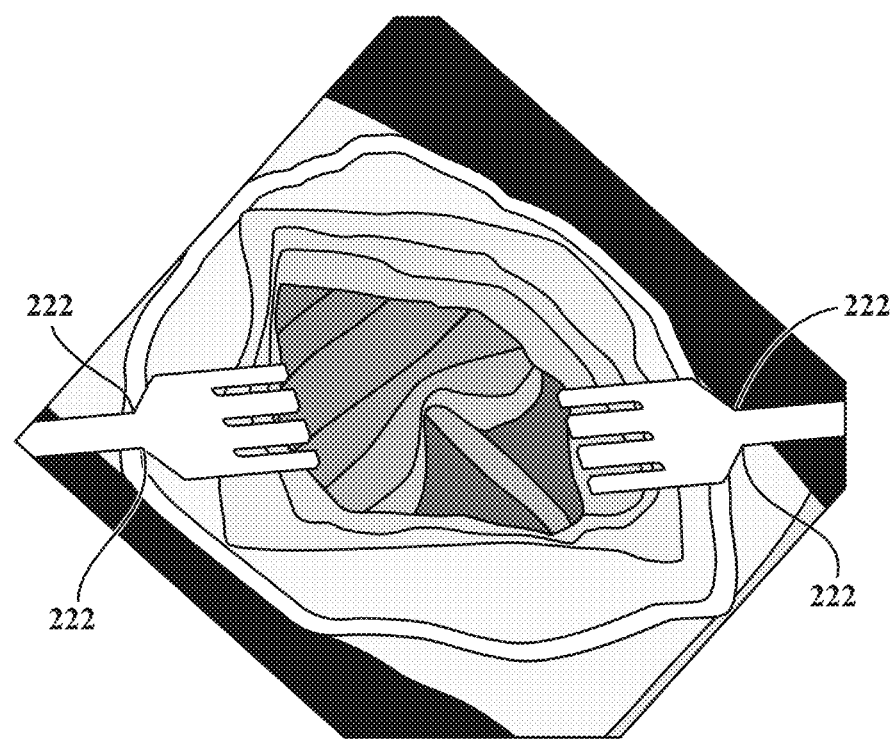
FIG. 15 is an illustration of an actual depth map subsequently captured by the vision device of FIG. 1.

For example, FIG. 15 illustrates an additional actual depth map subsequently generated by the vision device 40 after the actual depth map illustrated in FIG. 9 is generated. The position of the portion of the additional depth map in FIG. 15 representing the retractors 208 (FIG. 5) differs from the position of this portion in the depth map of FIG. 9, indicating the retractors 208 have moved. The navigation controller 22 may be configured to track such movement of the retractors 208 by monitoring for a changed position in the additional depth map relative to the previous actual depth map of a specific arrangement of features that is in the portion representing the retractors 208 and is positionally fixed relative to the rest of the retractors 208. For instance, the navigation controller 22 may monitor the additional depth map for a change in position of the arrangement of vertices 222 between the heads and bodies of the retractors 208.

Figure 16:
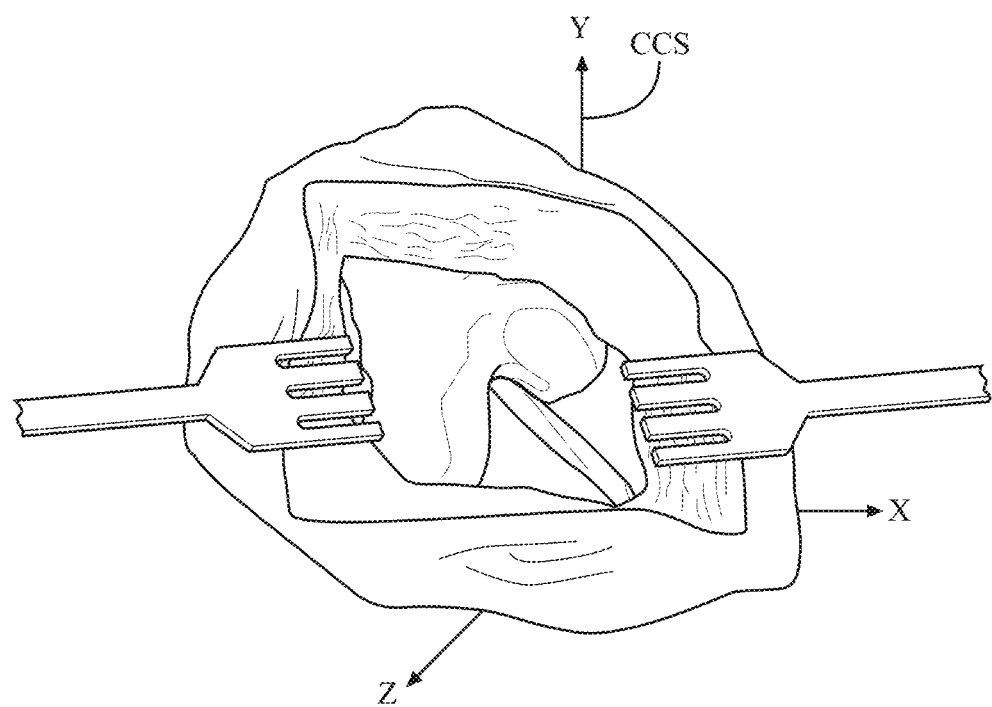
FIG. 16 is an illustration of the virtual models of FIG. 14 with updated positioning based on the actual depth map of FIG. 15.

Responsive to determining a change in position of the arrangement of vertices 222, the navigation controller 22 may be configured to determine an updated position of the retractors 208 in the common coordinate system based on the updated position of the arrangement of vertices 222 in the additional depth map of FIG. 15 and the fixed positional relationship between the arrangement of vertices 222 and the rest of the retractors 208. The navigation controller 22 may then be configured to adjust the virtual boundary associated with the retractors 208 in the common coordinate system based on the updated position. FIG. 16 illustrates an updated position of the virtual boundary for the retractors 208, namely the virtual model corresponding to the retractors 208, in the common coordinate system according to the new position of the arrangement of vertices 222 depicted in the additional depth map of FIG. 15.

Disclosed herein are systems and methods for tracking objects in a surgical workspace using a combination of machine vision and tracker-based localization. Due to the flexible nature of soft tissues such as muscle, skin, and ligaments, tracker-based localization is usually not adequate for tracking soft tissues. Accordingly, in addition to detecting the position of rigid objects in a surgical workspace using tracker-based localization, a surgical navigation system may include a vision device configured to generate a depth map of exposed surfaces in the surgical workspace. The surgical navigation system may further be configured to generate an expected depth map of the vision device based on a detected position of an object in the target site using localization, a virtual model corresponding to the object, and a positional relationship between the localizer and the vision device in a common coordinate system. The surgical navigation system may then be configured to identify a portion of the actual depth map that fails to match the estimated depth map, and to recognize objects, including soft tissues, in the target site based on the identified portion. The surgical navigation system may then be configured to determine whether the objects pose as obstacles to a current surgical plan.

In general, the routines executed to implement the embodiments of the invention, whether implemented as part of an operating system or a specific application, component, program, object, module or sequence of instructions, or even a subset thereof, may be referred to herein as "computer program code," or simply "program code." Program code typically comprises computer readable instructions that are resident at various times in various memory and storage devices in a computer and that, when read and executed by one or more processors in a computer, cause that computer to perform the operations necessary to execute operations and/or elements embodying the various aspects of the embodiments of the invention. Computer readable program instructions for carrying out operations of the embodiments of the invention may be, for example, assembly language or either source code or object code written in any combination of one or more programming languages.

Various program code described herein may be identified based upon the application within that it is implemented in specific embodiments of the invention. However, it should be appreciated that any particular program nomenclature that follows is used merely for convenience, and thus the invention should not be limited to use solely in any specific application identified and/or implied by such nomenclature. Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The program code embodied in any of the applications/modules described herein is capable of being individually or collectively distributed as a program product in a variety of different forms. In particular, the program code may be distributed using a computer readable storage medium having computer readable program instructions thereon for causing a processor to carry out aspects of the embodiments of the invention.

Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. A computer readable storage medium should not be construed as transitory signals per se (e.g., radio waves or other propagating electromagnetic waves, electromagnetic waves propagating through a transmission media such as a waveguide, or electrical signals transmitted through a wire). Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts, sequence diagrams, and/or block diagrams. The computer program instructions may be provided to one or more processors of a computer, a special purpose computer, or other programmable data processing apparatus to produce a machine, such that the instructions, which execute via the one or more processors, cause a series of computations to be performed to implement the functions, acts, and/or operations specified in the flowcharts, sequence diagrams, and/or block diagrams.

In certain alternative embodiments, the functions, acts, and/or operations specified in the flowcharts, sequence diagrams, and/or block diagrams may be re-ordered, processed serially, and/or processed concurrently consistent with embodiments of the invention. Moreover, any of the flowcharts, sequence diagrams, and/or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising".

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

The invention claimed is:

1. A navigation system comprising:
    a localizer configured to operate in a first spectral band to detect a position of a first object;
    a vision device configured to operate in a second spectral band to generate an actual depth map of surfaces near the first object, the second spectral band differing from the first spectral band; and
    a controller coupled to the localizer and the vision device, the controller configured to:
        access a virtual model corresponding to the first object;
        identify a positional relationship between the localizer and the vision device in a common coordinate system;
        generate an expected depth map of the vision device based on the detected position of the first object, the virtual model, and the positional relationship;
        identify a portion of the actual depth map that fails to match the expected depth map; and
        recognize a second object based on the identified portion.

2. The navigation system of claim 1, wherein the controller is configured to identify a position of the second object relative to the first object in the common coordinate system based on the detected position of the first object, a location of the second object in the actual depth map, and the positional relationship.

3. The navigation system of claim 2, wherein the first object defines a target volume of patient tissue to be treated according to a surgical plan, and the controller is configured to:
    determine whether the second object is an obstacle to treatment of the target volume according to the surgical plan based on the position of the second object relative to the target volume in the common coordinate system and the surgical plan; and
    responsive to determining that the second object is an obstacle to the surgical plan, perform one or more of: modify the surgical plan, trigger a notification, and halt surgical navigation.

4. The navigation system of claim 1, wherein a tracker is rigidly coupled to the first object, and the controller is configured to:
    detect, via the localizer, a position of the tracker in a first coordinate system specific to the localizer;
    identify a position of the virtual model in the first coordinate system based on the detected position of the tracker in the first coordinate system and a positional relationship between the tracker and the first object in the first coordinate system;
    transform the position of the virtual model in the first coordinate system to a position of the virtual model in a second coordinate system specific to the vision device based on the position of the virtual model in the first coordinate system and a positional relationship between the localizer and the vision device in the second coordinate system; and
    generate the expected depth map based on the position of the virtual model in the second coordinate system.

5. The navigation system of claim 1, wherein the controller is configured to identify a portion of the actual depth map that fails to match the expected depth map by being configured to:
    compute a difference between the actual depth map and the expected depth map;
    determine whether a first section of the difference indicates an absolute depth greater than a threshold depth; and
    identify as the portion a second section of the actual depth map that corresponds to the first section of the difference responsive to determining that the first section of the difference indicates an absolute depth greater than threshold depth, and wherein the threshold depth is non-zero.

6. The navigation system of claim 5, wherein the controller is configured to identify the portion of the actual depth map that fails to match the expected depth map by being configured to:
    determine whether a size of the first section is greater than a minimum size threshold; and
    identify as the portion the second section responsive to determining that the size of the first section is greater than the minimum size threshold.

7. The navigation system of claim 1, wherein the controller is configured to recognize the second object based on the identified portion by being configured to match the identified portion with a predetermined profile corresponding to the second object.

8. The navigation system of claim 1, wherein the portion of the actual depth map comprises an arrangement of features corresponding to the second object and located in a first position in the actual depth map, and the controller is configured to:
    track movement of the second object by being configured to monitor whether the arrangement of features moves to a second position that differs from the first position in an additional actual depth map subsequently generated by the vision device.

9. The navigation system of claim 1, wherein the controller is configured to generate a virtual boundary corresponding to the second object in the common coordinate system, the virtual boundary being configured to provide a constraint on a motion of a surgical tool.

10. The navigation system of claim 1, wherein the controller is configured to:
    crop the actual depth map to a region of interest based on the virtual model, the detected position of the first object, and the positional relationship between the localizer and the vision device in a common coordinate system; and identify a portion of the actual depth map that fails to match the expected depth map by being configured to compare the cropped actual depth map to the expected depth map.

11. The navigation system of claim 1, wherein the controller is configured to identify the positional relationship between the localizer and the vision device in the common coordinate system by being configured to:
  project a light pattern onto a surface in view of the localizer and the vision device;
  generate localization data using the localizer indicating a position of the light pattern in a first coordinate system specific to the localizer;
  receive a calibration depth map illustrating the projected light pattern generated by the vision device;
  identify a position of the projected light pattern in a second coordinate system specific to the vision device based on the calibration depth map; and
  identify the positional relationship between the localizer and the vision device in the common coordinate system based on the position of the light pattern in the first coordinate system and the position of the light pattern in the second coordinate system.

12. A method of operating a navigation system comprising a localizer configured to detect a position of a first object, a vision device configured to generate an actual depth map of surfaces near the first object, and a controller coupled to the localizer and the vision device, the method comprising the controller:
  accessing a virtual model corresponding to the first object;
  identifying a positional relationship between the localizer and the vision device in a common coordinate system;
  operating the localizer in a first spectral band for detecting the position of the first object;
  operating the vision device in a second spectral band for generating the actual depth map of the surfaces near the first object, the second spectral band differing from the first spectral band;
  generating an expected depth map of the vision device based on the detected position of the first object, the virtual model, and the positional relationship;
  identifying a portion of the actual depth map that fails to match the expected depth map; and
  recognizing a second object based on the identified portion.

13. The method of claim 12, further comprising the controller identifying a position of the second object relative to the first object the common coordinate system based on the detected position of the first object, a location of the second object in the actual depth map, and the positional relationship.

14. The method of claim 13, wherein the first object defines a target volume of patient tissue to be treated according to a surgical plan, and further comprising the controller:
  determining whether the second object is an obstacle to treating the target volume according to the surgical plan based on the position of the second object relative to the target volume in the common coordinate system and the surgical plan; and
  responsive to determining that the second object is an obstacle to the surgical plan, performing one or more of: modifying the surgical plan, triggering a notification, and halting surgical navigation.

15. The method of claim 12, wherein a tracker is rigidly coupled to the first object, and further comprising the controller:
  detecting, via the localizer, a position of the tracker in a first coordinate system specific to the localizer;
  identifying a position of the virtual model in the first coordinate system based on the detected position of the tracker in the first coordinate system and a positional relationship between the tracker and the first object in the first coordinate system;
  transforming the position of the virtual model in the first coordinate system to a position of the virtual model in a second coordinate system specific to the vision device based on the position of the virtual model in the first coordinate system and a positional relationship between the localizer and the vision device in the second coordinate system; and
  generating the expected depth map based on the position of the virtual model in the second coordinate system.

16. The method of claim 12, wherein identifying a portion of the actual depth map that fails to match the expected depth map comprises the controller:
  computing a difference between the actual depth map and the expected depth map;
  determining whether a first section of the difference indicates an absolute depth greater than a threshold depth; and
  identifying as the portion a second section of the actual depth map that corresponds to the first section of the difference responsive to determining that the first section of the difference indicates an absolute depth greater than a threshold depth, and wherein the threshold depth is non-zero.

17. The method of claim 16, wherein identifying a portion of the actual depth map that fails to match the expected depth map comprises the controller:
  determining whether a size of the first section is greater than a minimum size threshold; and
  identifying as the portion the second section responsive to the determining that the size of the first section is greater than the minimum size threshold.

18. The method of claim 12, wherein recognizing the second object based on the identified portion comprises the controller matching the identified portion with a predetermined profile corresponding to the second object.

19. The method of claim 12, wherein the portion of the actual depth map comprises an arrangement of features corresponding to the second object and located in a first position in the actual depth map, and further comprising the controller:
  tracking movement of the second object by monitoring whether the arrangement of features moves to a second position that differs from the first position in an additional actual depth map subsequently generated by the vision device.

20. The method of claim 12, comprising the controller generating a virtual boundary corresponding to the second object in the common coordinate system, the virtual boundary providing a constraint on a motion of a surgical tool.

21. The method of claim 12, comprising the controller:
  cropping the actual depth map to a region of interest based on the virtual model, the detected position of the first object, and the positional relationship between the localizer and the vision device in a common coordinate system; and
  identifying a portion of the actual depth map that fails to match the expected depth map by comparing the cropped actual depth map to the expected depth map.

22. The method of claim 12, wherein identifying the positional relationship between the localizer and the vision device in the common coordinate system comprises the controller:
projecting a light pattern onto a surface in view of the localizer and the vision device;
generating localization data using the localizer indicating a position of the light pattern in a first coordinate system specific to the localizer;
receiving a calibration depth map corresponding to the projected light pattern generated by the vision device;
identifying a position of the projected light pattern in a second coordinate system specific to the vision device based on the calibration depth map; and
identifying the positional relationship between the localizer and the vision device in the common coordinate system based on the position of the light pattern in the first coordinate system and the position of the light pattern in the second coordinate system.

23. A navigation system comprising:
a localizer configured to detect a position of a tracker in a first coordinate system specific to the localizer, the tracker being rigidly coupled to a first object;
a vision device configured to generate an actual depth map of surfaces near the first object; and
a controller coupled to the localizer and the vision device, the controller configured to:
access a virtual model corresponding to the first object;
identify a positional relationship between the localizer and the vision device in a common coordinate system;
identify a position of the virtual model in the first coordinate system based on the detected position of the tracker in the first coordinate system and a positional relationship between the tracker and the first object;
transform the position of the virtual model in the first coordinate system to a position of the virtual model in a second coordinate system specific to the vision device based on the position of the virtual model in the first coordinate system and the positional relationship between the localizer and the vision device;
generate an expected depth map based on the position of the virtual model in the second coordinate system;
identify a portion of the actual depth map that fails to match the expected depth map; and
recognize a second object based on the identified portion.

24. A navigation system comprising:
a localizer configured to detect a position of a first object;
a vision device configured to generate an actual depth map of surfaces near the first object; and
a controller coupled to the localizer and the vision device, the controller configured to:
access a virtual model corresponding to the first object;
identify a positional relationship between the localizer and the vision device in a common coordinate system;
generate an expected depth map of the vision device based on the detected position of the first object, the virtual model, and the positional relationship;
identify a portion of the actual depth map that fails to match the expected depth map;
recognize a second object based on the identified portion of the actual depth map, wherein the identified portion of the actual depth map comprises an arrangement of features corresponding to the second object and located in a first position in the actual depth map; and
track movement of the second object by being configured to monitor whether the arrangement of features moves to a second position that differs from the first position in an additional actual depth map subsequently generated by the vision device.

* * * * *